United States Patent
Jablonski et al.

(10) Patent No.: US 11,826,467 B2
(45) Date of Patent: Nov. 28, 2023

(54) W/O/W MICROEMULSIONS FOR OCULAR ADMINISTRATION

(71) Applicant: University of Tennessee Research Foundation, Knoxville, TN (US)

(72) Inventors: Monica M. Jablonski, Knoxville, TN (US); Mohamed Moustafa Ibrahim Moustafa, Knoxville, TN (US)

(73) Assignee: University of Tennessee Research Foundation, Knoxville, TN (US)

(*) Notice: Subject to any disclaimer, the term of this patent is extended or adjusted under 35 U.S.C. 154(b) by 0 days.

(21) Appl. No.: 16/955,659

(22) PCT Filed: Dec. 19, 2018

(86) PCT No.: PCT/US2018/066235
§ 371 (c)(1),
(2) Date: Jun. 18, 2020

(87) PCT Pub. No.: WO2019/126172
PCT Pub. Date: Jun. 27, 2019

(65) Prior Publication Data
US 2020/0383915 A1    Dec. 10, 2020

Related U.S. Application Data

(60) Provisional application No. 62/728,564, filed on Sep. 7, 2018, provisional application No. 62/607,429, filed on Dec. 19, 2017.

(51) Int. Cl.
| | | |
|---|---|---|
| *A61K 9/113* | (2006.01) | |
| *A61K 31/198* | (2006.01) | |
| *A61K 31/7056* | (2006.01) | |
| *A61K 47/14* | (2017.01) | |
| *A61K 47/32* | (2006.01) | |
| *A61K 9/00* | (2006.01) | |

(52) U.S. Cl.
CPC .......... *A61K 9/113* (2013.01); *A61K 31/198* (2013.01); *A61K 31/7056* (2013.01); *A61K 47/14* (2013.01); *A61K 47/32* (2013.01); *A61K 9/0048* (2013.01)

(58) Field of Classification Search
CPC .. A61K 9/113; A61K 31/198; A61K 31/7056; A61K 47/14; A61K 47/32; A61K 9/0048; A61K 31/197; A61K 31/195
See application file for complete search history.

(56) References Cited

U.S. PATENT DOCUMENTS

| | | | | |
|---|---|---|---|---|
| 5,656,280 | A * | 8/1997 | Herb ................... | A61K 8/0295 424/401 |
| 6,309,663 | B1 * | 10/2001 | Patel ................... | A61P 5/38 424/450 |
| 8,852,648 | B2 * | 10/2014 | Salamone ........... | A61K 31/395 424/618 |
| 2002/0077372 | A1 * | 6/2002 | Gers-Barlag ....... | A61Q 19/00 516/98 |

FOREIGN PATENT DOCUMENTS

| | | | |
|---|---|---|---|
| EP | 1867323 | 12/2007 | |
| JP | H10-330287 | 12/1998 | |
| JP | H11-033391 | 2/1999 | |
| JP | 2010-513449 A2 | 4/2010 | |
| WO | 2008/075102 | 6/2008 | |
| WO | WO-2015118320 A1 * | 8/2015 | ............. A61P 43/00 |

OTHER PUBLICATIONS

Eyecarenj, Glaucoma, obtained online at: https://www.eyecarenj.com/cataract-cornea-glaucoma-retina-plastics/glaucoma/#:~:text=Over%20the%20counter%20medicines%20such,to%20dangerously%20elevated%20eye%20pressure, downloaded on Apr. 11, 2023. (Year: 2023).*

Paik, Dong Won, Dong Hui Lim, and Tae-Young Chung. "Effects of taking pregabalin (Lyrica) on the severity of dry eye, corneal sensitivity and pain after laser epithelial keratomileusis surgery." British Journal of Ophthalmology 106.4 (2022): 474-479. (Year: 2022).*

Ibrahim, Mohamed Moustafa, et al. "Once daily pregabalin eye drops for management of glaucoma." ACS nano 13.12 (2019): 13728-13744. (Year: 2019).*

Doğan, Yusuf Emre, et al. "Pregabalin as a probable cause of central serous chorioretinopathy: Two case reports." Turkish journal of physical medicine and rehabilitation 67.4 (2021): 530. (Year: 2021).*

Hassan, Emad E. and Gallo, James M. A simple rheological method of the in vitro assessment of mucin-polymer bioadhesive bond strength. Pharmaceutical research 7(5):491-495, 1990.

International Search Report for PCT/US2018/066235 completed on Mar. 8, 2019 and dated Mar. 3, 2019.

Mayol et al. A novel poloxamers/hyaluronic acid in situ forming hydrogel for drug delivery: rheological, mucoadhesive and in vitro release properties. Eur J Pharm Biopharm 70(1):199-206, 2008.

Tayel et al. Promising ion-sensitive in situ ocular nanoemulsion gels of terbinafine hydrochloride: design, in vitro characterization and in vivo estimation of the ocular irritation and drug pharmacokinetics in the aqueous humor of rabbits. Int J Pharm 443(1-2):293-305 (2013).

International Preliminary Report on Patentability for PCT/US2018/066235 dated Jun. 23, 2020.

* cited by examiner

*Primary Examiner* — Abigail Vanhorn

(74) *Attorney, Agent, or Firm* — Fenwick & West LLP

(57) ABSTRACT

Microemulsions are disclosed herein that include a discontinuous internal phase comprising an aqueous solution encompassed within an internal emulsifier; a continuous oil phase encompassing the internal phase; and an external emulsifier encompassing the oil phase. Also disclosed are methods for the use of such microemulsions as drug delivery devices, and methods for treating glaucoma and reducing intraocular pressure.

39 Claims, 36 Drawing Sheets

Cumulative amount released (%) of pregabalin from different formulations

W/O/W MICROEMULSIONS FOR OCULAR ADMINISTRATION

CROSS REFERENCE

This application claims priority to U.S. provisional patent application Ser. No. 62/607,429 filed Dec. 19, 2017 and 62/728,564 filed Sep. 7, 2018, each incorporated by reference herein in its entirety.

BACKGROUND

Primary open angle glaucoma (POAG) accounts for 90% of glaucoma cases worldwide. It is a leading cause for irreversible blindness. POAG is characterized by progressive optic nerve damage arising from apoptotic cell death of retinal ganglion cells. Elevated intraocular pressure (IOP) is one of the most significant risk factors contributing to visual field loss in this disease. Steady-state IOP is generated by the balance of aqueous humor (AH) production by the ciliary body (CB) and AH drainage through the trabecular meshwork (TM; conventional pathway), and to a lesser degree the uveoscleral or nonconventional pathway. An imbalance between the inflow and outflow of AH leads to a change in IOP. Both POAG and IOP are highly heritable. In humans, IOP heritability is estimated to be ~55%. Moreover, the genetic risk of elevated IOP and POAG are partially shared, although some loci that are associated with POAG were not associated with IOP. Identification of gene variants that modulate IOP is therefore likely to provide critical insights and new targets for therapeutic intervention.

Because of the importance of a tightly maintained IOP, its reduction is the first-line treatment for glaucoma. Despite glaucoma prevalence and its impact on society, current medications do not address the underlying pathophysiologies that cause elevated IOP, nor do they address genetic variations related to IOP modulation. Moreover, because of their short half-life and low corneal residence time, they require multiple daily topical applications, which are associated with poor patient compliance.

SUMMARY

In one aspect, the disclosure provides microemulsions (ME), comprising:
(a) a discontinuous internal phase comprising an aqueous solution encompassed within an internal emulsifier;
(b) a continuous oil phase encompassing the internal phase; and
(c) an external emulsifier encompassing the oil phase.

In one embodiment, the ME further comprises (d) an aqueous phase surrounding the external emulsifier. In another embodiment, internal emulsifier is selected from the group consisting of propylene glycol monocaprylate or any other surfactant with a Hydrophile-Lipophile Balance (HLB) value 3-7 and/or propylene glycol ester of any fatty acid such as; propylene glycol monocaproate, propylene glycol monocaprylate, propylene glycol monocaprate, propylene glycol monolaurate, propylene glycol monostearate, propylene glycol monopalmitate, polyethylene glycol lauryl ether, polyethylene glycol oleyl ether, polyethylene glycol hexadecyl ether, sorbitan monopalmitate, sorbitan monostearate, sorbitan monooleate, sorbitan monolaurate, Transcutol® P (diethylene glycol monoethyl ether), Gelucire® 50/13 (mixture of PEG (MW 1500) mono-, di-, tri-esters of stearic acid), Gelucire® 44/14 (mixture of PEG (MW 1500) mono-, di-, tri-esters of lauric acid), Gelucire® 43/01 (mixture of PEG (MW 1500) mono-, di-, tri-esters of fatty acids $C_8$-$C_{18}$), any PEG mono-, di- and/or tri-esters of any fatty acid, lecithin, egg lecithin, phosphatidylcholine, phosphatidylethanolamine, phosphatidylinositol, tocopherol or any other phospholipid, and combinations thereof. In a further embodiment, the internal emulsifier is selected from the group consisting of Capryol® 90 (propylene glycol monoester of caprylic acid), lecithin, and combinations thereof.

In one embodiment, the aqueous solution is selected from the group consisting of deionized water, saline, phosphate buffered saline, artificial tears, balanced salt solution. In another embodiment, the oil phase is selected from the group consisting of an oil that consists of medium chain triglycerides of caprylic ($C_8$) and capric ($C_{10}$) acids, any pure fatty acid ester including but not limited to ethyl, propyl isopropyl, and butyl; esters of fatty acids including but not limited to caproic, caprylic, capric, lauric, palmitic, myristic, or stearic acids, isopropyl myristate, isopropyl palmitate, isopropyl caproate, isopropyl caprylate, ethyl stearate, butyl laurate, and any natural oil including but not limited to coconut oil, palm kernel oil, soya bean oil castor oil, cotton seed oil, corn oil, and olive oil; and combinations thereof. In a further embodiment, the oil phase comprises Labrafac™ lipophile WL 1349 (medium chain triglyceride of caprylic ($C_8$) and capric ($C_{10}$) acids).

In one embodiment, the external emulsifier is selected from the group consisting of caprylocaproyl polyoxyl-8 glycerides, macrogolglycerol ricinoleate, any other hydrophilic surfactant with a Hydrophile-Lipophile Balance (HLB) value between 10-16, polyethylene glycol mono- and/or di-esters of any fatty acid or fatty acid mixture, propylene glycol or any other alcohol including but not limited to glycerol, polyethylene glycol, ethanol, propanol, and isopropanol; and combinations thereof. In another embodiment, the external emulsifier comprises caprylocaproyl polyoxyl-8 glycerides, macrogolglycerol ricinoleate, propylene glycol, or combinations thereof.

In one embodiment, the ME contains 0.5-35% w/w aqueous solution, 0.5-95% w/w oil phase, and 5-99% w/w emulsifier. In another embodiment, the ME contains 10-30% w/w aqueous solution, 20-40% w/w oil phase, and 40-60% w/w emulsifier. In another embodiment, the ME contains at least 0.5% w/w aqueous solution, contains at least 1% w/w aqueous solution, contains at least 2% w/w aqueous solution, contains at least 3% w/w aqueous solution, contains at least 4% w/w aqueous solution, contains at least 5% w/w aqueous solution, contains at least 6% w/w aqueous solution, contains at least 7% w/w aqueous solution, contains at least 8% w/w aqueous solution, contains at least 9% w/w aqueous solution, contains at least 10% w/w aqueous solution, contains at least 11% w/w aqueous solution, contains at least 12% w/w aqueous solution, contains at least 13% w/w aqueous solution, contains at least 14% w/w aqueous solution, contains at least 15% w/w aqueous solution, contains at least 16% w/w aqueous solution, contains at least 17% w/w aqueous solution, contains at least 18% w/w aqueous solution, contains at least 19% w/w aqueous solution, contains at least 20% w/w aqueous solution, contains at least 25% w/w aqueous solution, contains at least 30% w/w aqueous solution, contains at least 35% w/w aqueous solution, contains at least 40% w/w aqueous solution, contains at least 45% w/w aqueous solution, contains at least 50% w/w aqueous solution, contains at least 55% w/w aqueous solution, contains at least 60% w/w aqueous solution, contains at least 65% w/w aqueous solution, contains at least 70% w/w aqueous solution, contains at least 75% w/w aqueous solution, contains at least 80% w/w aqueous solution, contains at least 85% w/w aqueous solution, contains at least 90% w/w aqueous solution, or contains at least 95% w/w aqueous solution.

In a further embodiment, the aqueous solution comprises a water-soluble drug. In various embodiments, the water soluble drug is selected from the group consisting of beta-blockers such as betaxolol and timolol; prostaglandin analogs such as bimatoprost, latanoprost, and travoprost; Alpha-adrenergic agents such as brimonidine tartrate; carbonic anhydrase inhibitors such as brinzolamide, dorzolamide, and acetazolamide; calcium channel blockers such as nimodipine and pregabalin; asialo, galactosylated, triantennary (NA3) (also known as asialo-, tri-antennary complex-type N-glycan), OT-551 hydrochloride (1-hydroxy-2,2,6,6-tetramethyl-4-piperidinyl cyclopropane carboxylic acid ester hydrochloride), brimonidine tartrate, clindamycin, ciprofloxacin, levofloxacin, gatifloxacin, gemifloxacin, ofloxacin, triamcinolone, valacyclovir, pyrimethamine, valganciclovir, ganciclovir, acyclovir, foscarnet, prednisolone acetate, diflupednate, triamcinolone, dexamethasone, methotrexate, azathioprine, mycophenolate mofetil, cyclosporine, tacrolimus, cyclophosphamide, ribavirin, bromfenac, ketorolac, nepafenac, lifitegrast, flubiprofen, diclonfenac, ketotifen, nedocromil, phenylephrine, azelastine, epinastine, naphazoline/pheniramine, oloptadine, bepotastine, alacaftadine, pemirolast, tetrahydrozoline with or without zinc sulfate, Iodoxamide, naphazoline, phenylephrine, cromolyn, emedastine, oxymetazoline, xylometazoline, loratidine, desloratidine, phenylglycine, gabapentin, combinations thereof, or pharmaceutically acceptable salts thereof. In another embodiment, the water-soluble drug is selected from the group consisting of phenylglycine, gabapentin, pregabalin and ribavirin, or a pharmaceutically acceptable salt thereof.

In one embodiment, the aqueous phase comprises a hydrogel. In another embodiment, the hydrogel comprises mucoadhesive polymers. In various further embodiments, the mucoadhesive polymers are selected from the group consisting of polyacrylic acid derivatives (including but not limited to CARBOPOL® (carbomer), such as CARBOPOL® 981 (carbomer homopolymer type A (allyl pentaerythritol crosslinked)), alginic acid and its salts or derivatives (including but not limited to sodium alginate), chitosan and its derivatives, dextran and its derivatives, pectin and its derivatives, gelatin and its derivatives, polyvinylpyrrolidone and its derivatives, N-methylpyrrolidone and its derivatives, hyaluronic acid salts and derivatives thereof, gellan gum and derivatives thereof, xanthan gum and derivatives thereof, agar and derivatives thereof, glycocholic acid and its salts or derivatives, or combinations thereof. In various other embodiments, the mucoadhesive polymers are selected from the group consisting of polyacrylic acid derivatives (including but not limited to CARBOPOL® (carbomer), such as CARBOPOL® 981 (carbomer homopolymer type A (allyl pentaerythritol crosslinked)), alginic acid and its salts or derivatives (including but not limited to sodium alginate), chitosan and its derivatives, or combinations thereof.

In one embodiment, the ME is present as globules between about 1 nm and about 200 nm in diameter. In another embodiment, the ME is formulated as a topical formulation.

In another aspect, the disclosure provides methods for reducing intraocular pressure (IOP), treating glaucoma, treating age-related macular degeneration (AMD), treating uveitis, and/or treating conjunctivitis, comprising administering to a subject with intraocular pressure, glaucoma, AMD, uveitis, and/or conjunctivitis an amount effective to reduce intraocular pressure, treat glaucoma, treat AMD, treat uveitis, and/or treat conjunctivitis of the ME of any embodiment or combinations disclosed herein, wherein the aqueous solution comprises a water soluble drug capable of reducing IOP, treating glaucoma, treating AMD, treating uveitis, and/or treating conjunctivitis. In various embodiments, the water soluble drug capable of reducing IOP, treating glaucoma, treating AMD, treating uveitis, and/or treating conjunctivitis is selected from the group consisting of beta-blockers such as betaxolol and timolol; prostaglandin analogs such as bimatoprost, latanoprost, and travoprost; Alpha-adrenergic agents such as brimonidine tartrate; carbonic anhydrase inhibitors such as brinzolamide, dorzolamide, and acetazolamide; calcium channel blockers such as nimodipine and pregabalin; asialo, galactosylated, triantennary (NA3) (also known as asialo-, tri-antennary complex-type N-glycan), OT-551 hydrochloride (1-hydroxy-2,2,6,6-tetramethyl-4-piperidinyl cyclopropane carboxylic acid ester hydrochloride), brimonidine tartrate, clindamycin, ciprofloxacin, levofloxacin, gatifloxacin, gemifloxacin, ofloxacin, triamcinolone, valacyclovir, pyrimethamine, valganciclovir, ganciclovir, acyclovir, foscarnet, prednisolone acetate, diflupednate, triamcinolone, dexamethasone, methotrexate, azathioprine, mycophenolate mofetil, cyclosporine, tacrolimus, cyclophosphamide, ribavirin, bromfenac, ketorolac, nepafenac, lifitegrast, flubiprofen, diclonfenac, ketotifen, nedocromil, phenylephrine, azelastine, epinastine, naphazoline/pheniramine, oloptadine, bepotastine, alacaftadine, pemirolast, tetrahydrozoline with or without zinc sulfate, Iodoxamide, naphazoline, phenylephrine, cromolyn, emedastine, oxymetazoline, xylometazoline, loratidine, desloratidine, phenylglycine, gabapentin, combinations thereof, or pharmaceutically acceptable salts thereof. In other embodiments, the water-soluble drug capable of reducing IOP, treating glaucoma, treating AMD, treating uveitis, and/or treating conjunctivitis is selected from the group consisting of phenylglycine, gabapentin, pregabalin and ribavirin, or a pharmaceutically acceptable salt thereof.

In one embodiment, the ME is administered to one or both eyes of the subject. In a further embodiment, the administering is done once per day.

In another aspect, the disclosure provides microemulsions (ME) comprising:

(a) a discontinuous (dispersed) oil phase; and
(b) an emulsifier encompassing the oil phase.

In one embodiment, the ME further comprises (c) a continuous aqueous phase surrounding the emulsifier. In a further embodiment, the ME comprises an insoluble or sparingly soluble drug in the discontinuous oil phase.

In a further aspect, the disclosure provides methods for treating glaucoma, comprising administering to a subject with glaucoma an amount effective to treat glaucoma of an inhibitor of Calcium Voltage-Gated Channel Auxiliary Subunit Alpha2delta 1 (CACNA2d1) protein. In one embodiment, the glaucoma is primary open angle glaucoma (POAG). In another aspect, the disclosure provides methods for reducing intraocular pressure, comprising administering to a subject in need thereof an amount effective to treat reduce intraocular pressure of an inhibitor of CACNA2d1 protein. In one embodiment of each of these aspects, the inhibitor comprises a gabapentanoid or phenylglycine. In one embodiment, the gabapentanoid comprises pregabalin. In a further embodiment, the inhibitor is administered topically. In another embodiment, the inhibitor is administered via eye drops.

DETAILED DESCRIPTION

Figure 1:
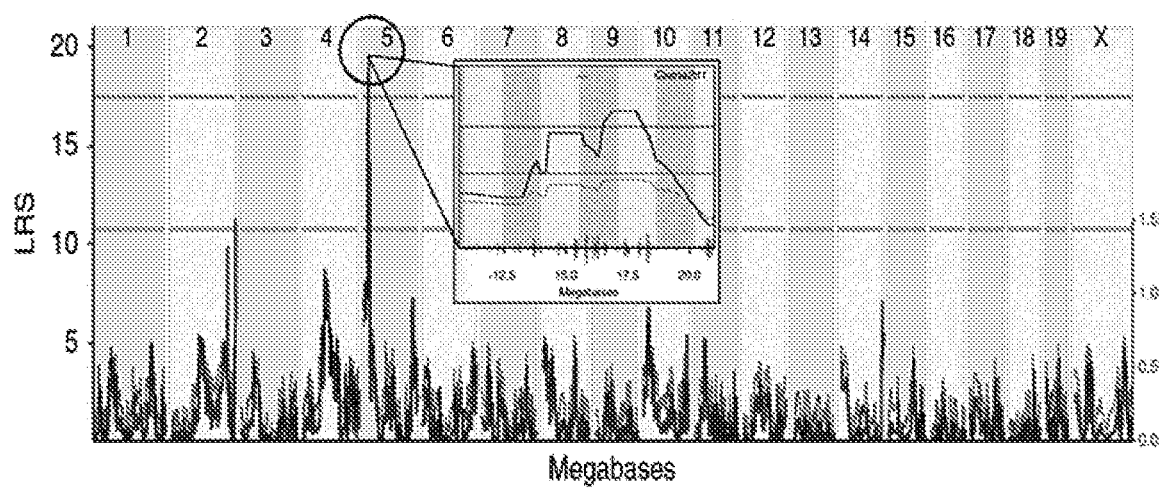
FIG. 1: Simple interval map of IOP revealed a single significant eQTL on proximal Chr 5. Cacna2d1 was identified as the top candidate that modulates IOP.

All references cited are herein incorporated by reference in their entirety.

As used herein, "about" means+/−5% of the recited parameter.

All embodiments of any aspect of the disclosure can be used in combination, unless the context clearly dictates otherwise.

In one aspect microemulsions (ME) are disclosed, comprising
  (a) a discontinuous internal phase comprising an aqueous solution encompassed within an internal emulsifier;
  (b) an oil phase encompassing the internal phase; and
  (c) an external emulsifier encompassing the oil phase.

As described herein, the inventors have developed novel microemulsions (ME) that can be used, for example, for topical delivery of water-soluble drugs. The microemulsions described herein are easy to synthesize, can be scaled to large batch sizes, are highly biocompatible and capable of extended drug release.

In one embodiment, the ME further comprise (d) an aqueous phase surrounding the external emulsifier. In this embodiment, a water soluble drug that is present in the aqueous layer must pass through 2 interfaces, the inner w/o interface (i.e.: aqueous solution through the internal emulsifier) and the outer o/w interface (i.e.: oil phase through the external emulsifier), after which it has to diffuse through the aqueous phase (including but not limited to a viscous hydrogel) to be ready for absorption at a site of administration. Because of this engineering, the time required for the drug to pass through all these stages is greatly prolonged, allowing for sustained release.

Any suitable hydrophobic internal emulsifier may be used in the MEs. In various non-limiting embodiments, the internal emulsifier is selected from the group consisting of propylene glycol monocaprylate or any other surfactant with an Hydrophile-Lipophile Balance (HLB) value 3-7 and/or propylene glycol ester of any fatty acid such as; propylene glycol monocaproate, propylene glycol monocaprylate, propylene glycol monocaprate, propylene glycol monolaurate, propylene glycol monostearate, propylene glycol monopalmitate, polyethylene glycol lauryl ether, polyethylene glycol oleyl ether, polyethylene glycol hexadecyl ether, sorbitan monopalmitate, sorbitan monostearate, sorbitan monooleate, sorbitan monolaurate, Transcutol® P (diethylene glycol monoethyl ether), Gelucire® 50/13 (mixture of PEG (MW 1500) mono-, di-, tri-esters of stearic acid), Gelucire® 44/14 (mixture of PEG (MW 1500) mono-, di-, tri-esters of lauric acid), Gelucire® 43/01 (mixture of PEG (MW 1500) mono-, di-, tri-esters of fatty acids $C_8$-$C_{18}$), any PEG (polyethylene glycol) mono-, di- and/or tri-esters of any fatty acid, lecithin, egg lecithin, phosphatidylcholine, phosphatidylethanolamine, phosphatidylinositol, tocopherol or any other phospholipid, and combinations thereof.

Capryol® 90 (propylene glycol monoester of caprylic acid) is a surfactant with HLB=5. Its chemical name is propylene glycol monocaprylate (propylene glycol monoester of caprylic acid). Alternatives to propylene glycol monocaprylate may be any other surfactant with an HLB value 3-7 and/or propylene glycol ester of any fatty acid such as propylene glycol monocaproate, propylene glycol monocaprylate, propylene glycol monocaprate, propylene glycol monolaurate, propylene glycol monostearate, propylene glycol monopalmitate, polyethylene glycol lauryl ether, polyethylene glycol oleyl ether, polyethylene glycol hexadecyl ether, sorbitan monopalmitate, sorbitan monostearate, sorbitan monooleate, sorbitan monolaurate, etc.

Labrasol is a hydrophilic surfactant with HLB value=12. It consists of a small fraction of mono-, di- and triglycerides and mainly polyethylene glycol-8 (MW 400) mono- and diesters of caprylic and capric acids. Its chemical name is caprylocaproyl polyoxyl-8 glycerides, caprylocaproyl macrogol-8 glycerides or PEG-8 caprylic/capric glycerides. Its alternatives may be any other hydrophilic surfactant with HLB value (10-14) and/or polyethylene glycol mono- and/or di-esters of any fatty acid.

Cremophor EL is a hydrophilic surfactant with HLB value=14. Its chemical names are macrogolglycerol ricinoleate, PEG-35 castor oil, Polyoxyl 35 hydrogenated castor oil, or Polyoxyl-35 castor oil. Alternatives may be any other hydrophilic surfactant with HLB value (12-16) and/or polyethylene glycol mono- and/or di-esters of any fatty acid or fatty acid mixture.

Lecithin is a hydrophobic surfactant with HLB value=4-7. Its chemical name is 2-nonanoyloxy-3-octadeca-9,12-dienoyloxypropoxy)-[2-(trimethylazaniumyl)ethyl]phosphinate. It is a mixture of natural phospholipids so its alternatives may be one of the following: egg lecithin, phosphatidylcholine, phosphatidylethanolamine, phosphatidylinositol, tocopherol or any other phospholipid.

In one embodiment, the internal emulsifier is selected from the group consisting of propylene glycol monocaprylate, lecithin, and combinations thereof.

Any suitable aqueous solution may be used in the MEs. In various non-limiting embodiments, the aqueous solution is selected from the group consisting of deionized water, saline, phosphate buffered saline, artificial tears, and balanced salt solution.

Any suitable oil phase may be used in the MEs. In various non-limiting embodiments, the oil phase is selected from the group consisting of an oil that consists of medium chain triglycerides of caprylic ($C_8$) and capric ($C_{10}$) acids, any pure fatty acid ester including but not limited to ethyl, propyl, isopropyl, and butyl; esters of fatty acids including but not limited to caproic, caprylic, capric, lauric, palmitic, myristic, or stearic acids, isopropyl myristate, isopropyl palmitate, isopropyl caproate, isopropyl caprylate, ethyl stearate, butyl laurate, and any natural oil including but not limited to coconut oil, palm kernel oil, soya bean oil, castor oil, cotton seed oil, corn oil, and olive oil; and combinations thereof. In one specific embodiment, the oil phase comprises Labrafac™ lipophile WL1349 (i.e., triglyceride esters of caprylic and capric acids).

Any suitable external emulsifier may be used in the MEs. In various other embodiments, the external emulsifier is selected from the group consisting of caprylocaproyl polyoxyl-8 glycerides, macrogolglycerol ricinoleate, any other hydrophilic surfactant with Hydrophile-Lipophile Balance (HLB) value between 10-16, polyethylene glycol mono- and/or di-esters of any fatty acid or fatty acid mixture, propylene glycol or any other alcohol including but not limited to glycerol, polyethylene glycol, ethanol, propanol, and isopropanol; and combinations thereof. In various further embodiments, the external emulsifier comprises caprylocaproyl polyoxyl-8 glycerides, macrogolglycerol ricinoleate, propylene glycol, or combinations thereof.

Any suitable combinations of the various components of the MEs of the disclosure may be used. In one embodiment, the ME contains 0.5-35% w/w aqueous solution, 0.5-95% w/w oil phase, and 5-99% w/w emulsifier (i.e.: internal emulsifier+external emulsifier). In another embodiment, the ME contains 10-30% w/w aqueous solution, 20-40% w/w oil phase, and 40-60% w/w emulsifier. In a further embodiment, the ME contains about 20% w/w aqueous solution, about 30% w/w oil phase, and about 50% w/w emulsifier. In various further embodiments, the ME contains at least 0.5% w/w aqueous solution, contains at least 1% w/w aqueous solution, contains at least 2% w/w aqueous solution, contains at least 3% w/w aqueous solution, contains at least 4% w/w aqueous solution, contains at least 5% w/w aqueous solution, contains at least 6% w/w aqueous solution, contains at least 7% w/w aqueous solution, contains at least 8% w/w aqueous solution, contains at least 9% w/w aqueous solution, contains at least 10% w/w aqueous solution, contains at least 11% w/w aqueous solution, contains at least 12% w/w aqueous solution, contains at least 13% w/w aqueous solution, contains at least 14% w/w aqueous solution, contains at least 15% w/w aqueous solution, contains at least 16% w/w aqueous solution, contains at least 17% w/w aqueous solution, contains at least 18% w/w aqueous solution, contains at least 19% w/w aqueous solution, contains at least 20% w/w aqueous solution, contains at least 25% w/w aqueous solution, contains at least 30% w/w aqueous solution, contains at least 35% w/w aqueous solution, contains at least 40% w/w aqueous solution, contains at least 45% w/w aqueous solution, contains at least 50% w/w aqueous solution, contains at least 55% w/w aqueous solution, contains at least 60% w/w aqueous solution, contains at least 65% w/w aqueous solution, contains at least 70% w/w aqueous solution, contains at least 75% w/w aqueous solution, contains at least 80% w/w aqueous solution, contains at least 85% w/w aqueous solution, contains at least 90% w/w aqueous solution, or contains at least 95% w/w aqueous solution.

In various embodiments, the external emulsifier is present in a ratio between about 10:1 and about 2:1 relative to the internal emulsifier. In various further embodiments, the external emulsifier is present in a ratio between about 9:1 and about 2:1, between about 8:1 and about 2:1, between about 7:1 and about 2:1, between about 6:1 and about 2:1, between about 5:1 and about 2:1, between about 4:1 and about 2:1, between about 3:1 and about 2:1, between about 10:1 and about 2.5:1, between about 9:1 and about 2.5:1, between about 8:1 and about 2.5:1, between about 7:1 and about 2.5:1, between about 6:1 and about 2.5:1, between about 5:1 and about 2.5:1, between about 4:1 and about 2.5:1, between about 3:1 and about 2.5:1, between about 10:1 and about 3:1 relative to the internal emulsifier, between about 9:1 and about 3:1, between about 8:1 and about 3:1, between about 7:1 and about 3:1, between about 6:1 and about 3:1, between about 5:1 and about 3:1, between about 4:1 and about 3:1, between about 10:1 and about 4:1 relative to the internal emulsifier, between about 9:1 and about 4:1, between about 8:1 and about 4:1, between about 7:1 and about 4:1, between about 6:1 and about 4:1, between about 5:1 and about 4:1, between about 10:1 and about 5:1 relative to the internal emulsifier, between about 9:1 and about 5:1, between about 8:1 and about 5:1, between about 7:1 and about 5:1, between about 6:1 and about 5:1, relative to the internal emulsifier.

In one embodiment, the aqueous solution comprises a water soluble therapeutic. Any suitable water soluble therapeutic may be incorporated in the aqueous solution, including but not limited to beta-blockers such as betaxolol and timolol; prostaglandin analogs such as bimatoprost, latanoprost, and travoprost; Alpha-adrenergic agents such as brimonidine tartrate; carbonic anhydrase inhibitors such as brinzolamide, dorzolamide, and acetazolamide; calcium channel blockers such as nimodipine and pregabalin; asialo, galactosylated, triantennary (NA3) (also known as asialo-, tri-antennary complex-type N-glycan), OT-551 hydrochloride (1-hydroxy-2,2,6,6-tetramethyl-4-piperidinyl cyclopropane carboxylic acid ester hydrochloride), brimonidine tartrate, clindamycin, ciprofloxacin, levofloxacin, gatifloxacin, gemifloxacin, ofloxacin, triamcinolone, valacyclovir, pyrimethamine, valganciclovir, ganciclovir, acyclovir, foscarnet, prednisolone acetate, diflupednate, triamcinolone, dexamethasone, methotrexate, azathioprine, mycophenolate mofetil, cyclosporine, tacrolimus, cyclophosphamide, ribavirin, bromfenac, ketorolac, nepafenac, lifitegrast, flubiprofen, diclonfenac, ketotifen, nedocromil, phenylephrine, azelastine, epinastine, naphazoline/pheniramine, oloptadine, bepotastine, alacaftadine, pemirolast, tetrahydrozoline with or without zinc sulfate, Iodoxamide, naphazoline, phenylephrine, cromolyn, emedastine, oxymetazoline, xylometazoline, loratidine, desloratidine, phenylglycine, gabapentin, or combinations thereof. In specific embodiments, the water-soluble drug is selected from the group consisting of phenylglycine, gabapentin, pregabalin and ribavirin, or a pharmaceutically acceptable salt thereof.

In another embodiment, the aqueous phase comprises a hydrogel (i.e.: a gel or swollen network structured polymer matrix in which the liquid component is water or aqueous solution, emulsion or suspension). In one embodiment, the hydrogel comprises mucoadhesive polymers. Any suitable mucoadhesive polymers may be used, including but not limited to polyacrylic acid derivatives (including but not limited to CARBOPOL® (carbomer), such as CARBOPOL® 981 (carbomer homopolymer type A (allyl pentaerythritol crosslinked)), alginic acid and its salts or derivatives (including but not limited to sodium alginate), chitosan and its derivatives, dextran and its derivatives, pectin and its derivatives, gelatin and its derivatives, polyvinylpyrrolidone and its derivatives, N-methylpyrrolidone and its derivatives, hyaluronic acid salts and derivatives thereof, gellan gum and derivatives thereof, xanthan gum and derivatives thereof, agar and derivatives thereof, glycocholic acid and its salts or derivatives, or combinations thereof. In specific embodiments, the mucoadhesive polymers are selected from the group consisting of polyacrylic acid derivatives (including but not limited to CARBOPOL® (carbomer), such as CARBOPOL® 981 (carbomer homopolymer type A (allyl pentaerythritol crosslinked)), alginic acid and its salts or derivatives (including but not limited to sodium alginate), chitosan and its derivatives, or combinations thereof.

The ME may be formulated for any suitable route of administration (i.e.: orally, topically, intranasally, etc.), in dosage unit formulations of water soluble therapeutic loaded in the ME. The formulation may include any other components suitable for a desired administrative route, including but not limited to conventional pharmaceutically acceptable carriers, adjuvants, and vehicles. In one embodiment, the ME is formulated as a topical formulation, such as for delivery to the eye.

The MEs disclosed herein may be provided as ME globules (i.e., drops). ME globules may be of any suitable size. In one embodiment, the ME globule is between about 1 nm and about 200 nm in diameter. In various further embodiments, ME globules are between about 1 nm and about 150 nm, about 1 nm and about 100 nm, about 1 nm and about 50 nm, about 1 nm and about 20 nm, about 1 nm and about 18 nm, about 1 nm and about 17 nm, about 5 nm and about 200 nm, about 5 nm and about 150 nm, about 5 nm and about 100 nm, about 5 nm and about 50 nm, about 5 nm and about 20 nm, about 5 nm and about 18 nm, about 5 nm and about 17 nm in diameter. In various further embodiments, the ME globules are about 1 nm, about 2 nm, about 3 nm, about 4 nm, about 5 nm, about 6 nm, about 7 nm, about 8 nm, about 9 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 90 nm, about 95 nm, about 100 nm, about 110 nm, about 120 nm, about 130 nm, about 140 nm, about 150 nm, about 160 nm, about 170 nm, about 180 nm, about 190 or about 200 nm in diameter. In other embodiments, the ME globules are at least about 1 nm, at least 2 nm, at least 3 nm, at least 4 nm, at least 5 nm, at least 6 nm, at least 7 nm, at least 8 nm, at least 9 nm, at least 10 nm, at least 15 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 90 nm, at least 95 nm, at least 100 nm, at least 110 nm, at least 120 nm, at least 130 nm, at least 140 nm, at least 150 nm, at least 160 nm, at least 170 nm, at least 180 nm, at least 190 or at least 200 nm in diameter.

In another aspect is provided methods for treating an eye disease comprising administering to a subject in need thereof an amount effective to treat the eye disease of the ME of any embodiment or combination of embodiments described herein, wherein the aqueous solution comprises a water soluble therapeutic capable of treating the eye disease. In various embodiments, the methods are for reducing intraocular pressure (IOP), treating glaucoma, treating age-related macular degeneration (AMD), treating uveitis, and/or treating conjunctivitis, comprising administering to a subject with elevated intraocular pressure, glaucoma, AMD, uveitis, and/or conjunctivitis an amount effective to reduce intraocular pressure, treat glaucoma, treat AMD, treat uveitis, and/or treat conjunctivitis of the ME of any embodiment or combination of embodiments described herein, wherein the aqueous solution comprises a water soluble therapeutic capable of reducing IOP, treating glaucoma, treating AMD, treating uveitis, and/or treating conjunctivitis. In various embodiments, the water soluble therapeutic capable of reducing IOP, treating glaucoma, treating AMD, treating uveitis, and/or treating conjunctivitis is selected from the group consisting of beta-blockers such as betaxolol and timolol; prostaglandin analogs such as bimatoprost, latanoprost, and travoprost; Alpha-adrenergic agents such as brimonidine tartrate; carbonic anhydrase inhibitors such as brinzolamide, dorzolamide, and acetazolamide; calcium channel blockers such as nimodipine and pregabalin; asialo, galactosylated, triantennary (NA3) (also known as asialo-, tri-antennary complex-type N-glycan), OT-551 hydrochloride (1-hydroxy-2,2,6,6-tetramethyl-4-piperidinyl cyclopropane carboxylic acid ester hydrochloride), brimonidine tartrate, clindamycin, ciprofloxacin, levofloxacin, gatifloxacin, gemifloxacin, ofloxacin, triamcinolone, valacyclovir, pyrimethamine, valganciclovir, ganciclovir, acyclovir, foscarnet, prednisolone acetate, diflupednate, triamcinolone, dexamethasone, methotrexate, azathioprine, mycophenolate mofetil, cyclosporine, tacrolimus, cyclophosphamide, ribavirin, bromfenac, ketorolac, nepafenac, lifitegrast, flubiprofen, diclonfenac, ketotifen, nedocromil, phenylephrine, azelastine, epinastine, naphazoline/pheniramine, oloptadine, bepotastine, alacaftadine, pemirolast, tetrahydrozoline with or without zinc sulfate, Iodoxamide, naphazoline, phenylephrine, cromolyn, emedastine, oxymetazoline, xylometazoline, loratidine, desloratidine, phenylglycine, gabapentin, or combinations thereof. In specific embodiments, the water soluble drug capable of reducing IOP, treating glaucoma, treating AMD, treating uveitis, and/or treating conjunctivitis is selected from the group consisting of phenylglycine, gabapentin, pregabalin and ribavirin, or a pharmaceutically acceptable salt thereof. In one specific embodiment, the water soluble drug capable of reducing IOP, treating glaucoma, treating AMD, treating uveitis, and/or treating conjunctivitis is pregabalin, and the pregabalin is present in the ME at between about 0.2% to about 2% of the ME % w/w; in various further embodiments, the pregabalin is present in the ME at between about 0.2% to about 1.5%, between about 0.2% to about 1%, between about 2% to about 0.75%, between about 0.3% to about 2%, between about 0.3% to about 1.5%, between about 0.3% to about 1%, between about 0.3% to about 0.75%, between about 0.4% to about 2%, between about 0.4% to about 1.5%, between about 0.4% to about 1%, between about 0.4% to about 0.75%, between about 0.5% to about 2%, between about 0.5% to about 1.5%, between about 0.5% to about 1%, between about 0.5% to about 0.75%, between about 0.2% to about 0.6%, between about 0.3% to about 0.6%, between about 0.4% to about 0.6%, between about 0.5% to about 0.6% about 0.2%, about 0.3%, about 0.4%, about 0.5%, or about 0.6% of the ME % w/w. The MEs described herein are excellent drug delivery systems for any water-soluble therapeutic candidate.

In other aspects of this embodiment, a water-soluble drug disclosed herein is used to reduce IOP and/or treat glaucoma (including POAG), AMD, uveitis, and/or conjunctivitis in a patient suffering from one or more of these syndromes by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a water-soluble drug disclosed herein reduces IOP and/or treats glaucoma, AMD, uveitis, and/or conjunctivitis in a patient suffering from one of these syndromes from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

An ME disclosed herein may comprise a water-soluble drug in an amount sufficient to allow customary administration to an individual. In aspects of this embodiment, a ME disclosed herein may include, e.g., at least 0.3% w/w, at least 0.4% w/w, 0.5% w/w, at least 0.6% w/w, at least 0.7% w/w, at least 0.8% w/w, at least 0.9% w/w, at least 1.0% w/w, at least 1.1% w/w, at least 1.2% w/w of a water-soluble drug. In yet other aspects of this embodiment, a ME disclosed herein may include, e.g., about 0.3% w/w to about 1.2% w/w, about 0.3% w/w to about 1.1% w/w, about 0.3% w/w to about 1.0% w/w, about 0.3% w/w to about 0.9% w/w, about 0.3% w/w to about 0.8% w/w, about 0.4% w/w to about 1% w/w, about 0.4% w/w to about 0.9% w/w, about 0.4% w/w to about 0.8% w/w, about 0.4% w/w to about 0.7% w/w, about 0.5% w/w to about 1.0% w/w, about 0.5% w/w to about 0.9% w/w, about 0.5% w/w to about 0.8% w/w, about 0.5% w/w to about 0.7% w/w, about 0.55% w/w to about 0.8% w/w, or about 0.55% w/w to about 0.7% w/w of a water-soluble drug.

The final concentration of a water-soluble drug disclosed herein in a ME disclosed herein may be of any concentration desired. In an aspect of this embodiment, the final concentration of a water-soluble drug in a ME may be a therapeutically effective amount. In other aspects of this embodiment, the final concentration of a water-soluble drug in a ME may be, e.g., at least 0.3% w/w, at least 0.4% w/w, 0.5% w/w, at least 0.6% w/w, at least 0.7% w/w, at least 0.8% w/w, at least 0.9% w/w, at least 1.0% w/w, at least 1.1% w/w, at least 1.2% w/w. In other aspects of this embodiment, the concentration of a water-soluble drug disclosed herein in a ME may be, e.g., at most 0.3% w/w, at most 0.4% w/w, at most 0.5% w/w, at most 0.6% w/w, at most 0.7% w/w, at most 0.8% w/w, at most 0.9% w/w, at most 1.0% w/w, at most 1.1% w/w, or at most 1.2% w/w. In other aspects of this embodiment, the final concentration of a water-soluble drug in a ME may be in a range of, e.g., bout 0.3% w/w to about 1.2% w/w, about 0.3% w/w to about 1.1% w/w, about 0.3% w/w to about 1.0% w/w, about 0.3% w/w to about 0.9% w/w, about 0.3% w/w to about 0.8% w/w, about 0.4% w/w to about 1% w/w, about 0.4% w/w to about 0.9% w/w, about 0.4% w/w to about 0.8% w/w, about 0.4% w/w to about 0.7% w/w, about 0.5% w/w to about 1.0% w/w, about 0.5% w/w to about 0.9% w/w, about 0.5% w/w to about 0.8% w/w, about 0.5% w/w to about 0.7% w/w, about 0.55% w/w to about 0.8% w/w, or about 0.55% w/w to about 0.7% w/w.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s). Certain embodiments of the present specification disclose, in part, treating an individual suffering from IOP, glaucoma, AMD, uveitis, and/or conjunctivitis. In these embodiments, treating may refer to reducing or eliminating in an individual a clinical symptom of IOP, glaucoma, AMD, uveitis, and/or conjunctivitis; or delaying or preventing in an individual the onset of a clinical symptom of IOP, glaucoma, AMD, uveitis, and/or conjunctivitis. For example, the term "treating" can mean reducing a symptom of a condition characterized by a IOP, glaucoma, AMD, uveitis, and/or conjunctivitis, by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with IOP, glaucoma, AMD, uveitis, and/or conjunctivitis are well known and can be determined by a person of ordinary skill in the art by taking into account various factors associated with each of these syndromes. Those of skill in the art will know the appropriate symptoms or indicators associated with IOP, glaucoma, AMD, uveitis, and/or conjunctivitis and will know how to determine if an individual is a candidate for treatment as disclosed herein.

In various embodiments, a therapeutically effective amount of a water-soluble drug disclosed herein reduces a symptom associated with IOP, glaucoma, AMD, uveitis, and/or conjunctivitis by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other embodiments, a therapeutically effective amount of a water-soluble drug disclosed herein reduces a symptom associated with IOP, glaucoma, AMD, uveitis, and/or conjunctivitis by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other embodiments, a therapeutically effective amount of a water-soluble drug disclosed herein reduces a symptom associated with IOP, glaucoma, AMD, uveitis, and/or conjunctivitis by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

The therapeutics (such as the MEs) for use in the methods disclosed herein may be administered as deemed appropriate by attending medical personnel. In one embodiment, the therapeutics for use in the methods disclosed herein (such as the ME) are administered to one or both eyes of the subject. In another embodiment, the administering is done once per day. Dosing can be single dosage or cumulative (serial dosing), and can be readily determined by one skilled in the art. For instance, treatment of IOP, glaucoma, AMD, uveitis, and/or conjunctivitis may comprise a one-time administration of an effective dose of a ME containing a water-soluble drug disclosed herein. Alternatively, treatment of IOP, glaucoma, AMD, uveitis, and/or conjunctivitis may comprise multiple administrations of an effective dose of a ME containing a water-soluble drug carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a ME containing a water-soluble drug disclosed herein can be administered to an individual once daily for an indefinite period of time, or until the individual no longer requires therapy. A person of ordinary skill in the art will recognize that the condition of the individual can be monitored throughout the course of treatment and that the effective amount of a ME containing a water-soluble drug disclosed herein that is administered can be adjusted accordingly.

In various embodiments, a sustained release water-soluble drug delivery platform releases a water-soluble drug disclosed herein with substantially zero order release kinetics over a period of, e.g., about 7 days after administration, about 15 days after administration, about 30 days after administration, about 45 days after administration, about 60 days after administration, about 75 days after administration, or about 90 days after administration. In other embodiments, a sustained release water-soluble drug delivery platform releases a water-soluble drug disclosed herein with substantially zero order release kinetics over a period of, e.g., at least 7 days after administration, at least 15 days after administration, at least 30 days after administration, at least 45 days after administration, at least 60 days after administration, at least 75 days after administration, or at least 90 days after administration.

In a further embodiment, a water-soluble drug of the present invention and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, the period of administration of a therapeutic for the treatment of IOP, glaucoma, AMD, uveitis, and/or conjunctivitis is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped between period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In various embodiments, a water-soluble drug delivery platform releases a therapeutic disclosed herein with substantially zero order release kinetics over a period of, e.g., about 1 day after administration, about 2 days after administration, about 3 days after administration, about 4 days after administration, about 5 days after administration, or about 6 days after administration. In other aspects of this embodiment, a water-soluble drug delivery platform releases a therapeutic disclosed herein with substantially zero order release kinetics over a period of, e.g., at most 1 day after administration, at most 2 days after administration, at most 3 days after administration, at most 4 days after administration, at most 5 days after administration, or at most 6 days after administration.

In various embodiments, a therapeutically effective amount of a ME containing a water-soluble drug disclosed herein reduces internal pressure within the eye of an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a ME containing a water-soluble drug disclosed herein reduces internal pressure within the eye in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a Me containing a water-soluble drug disclosed herein reduces internal pressure within the eye in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

As used herein, the term "subject", "individual," or "patient," used interchangeably, refer to any animal, including mammals, such as mice, rats, other rodents, rabbits, dogs, cats, birds, swine, horses, livestock (e.g., pigs, sheep, goats, cattle), primates or humans. In specific embodiments, the subject, individual, or patient is a human. A pharmaceutical composition that includes a ME and a water-soluble drug is administered to a subject. Typically, any subject who is a candidate for treatment is a candidate with some form of IOP, glaucoma, AMD, uveitis, and/or conjunctivitis. Pre-operative evaluation typically includes routine history and physical examination in addition to thorough informed consent disclosing all relevant risks and benefits of the procedure.

The therapeutic-containing MEs for use in the methods disclosed herein can be formulated for and administered via any suitable route, including but not limited to oral, intravenous, intravaginal, intra-anal, subcutaneous, intracranial, topical, intramuscular, enteral or parenteral routes of administration. In specific embodiments, the therapeutic-containing MEs can be formulated for and administered via topical administration for ocular or optic application (including but not limited to being formulated as eye drops), intranasal administration, orally for different systemic diseases, transdermal application for systemic diseases and topically for different skin disorders. The MEs described herein can also be used as a drug delivery system to incorporate one or more water-soluble compounds of any type, including but not limited to small molecules and peptides, in a single ME.

Preparation of the ME may be carried out under any suitable conditions as appropriate for an intended use. In one non-limiting embodiment, preparation of the MW may be carried out at room temperature, in order to allow a water-soluble drug to dissolve fully in the pharmaceutically acceptable solvent. However, in other embodiments of the method, preparation of the ME may be carried out at a temperature that is greater than room temperature. In aspects of this embodiment, preparation of the ME may be carried out at a temperature that is, e.g., greater than 21° C., greater than 25° C., greater than 30° C., greater than 35° C. or greater than 37° C., greater than 40° C., greater than 42° C., greater than 45° C., greater than 50° C., greater than 55° C., or greater than 60° C. In aspects of this embodiment, preparation of the ME may be carried out at a temperature that is between, e.g., about 20° C. to about 30° C., about 25° C. to about 35° C., about 30° C. to about 40° C., about 35° C. to about 45° C., about 40° C. to about 50° C., about 45° C. to about 55° C., or about 50° C. to about 60° C. In certain cases, preparation of the ME may be carried out at temperatures below room temperature, in order to allow a therapeutic to dissolve fully in solvent. However, in other embodiments of the method, preparation of the ME may be carried out at a temperature that is less than room temperature, e.g., less than 10° C., greater than 5° C., greater than 0° C., greater than −10° C. or greater than −20° C.

In an embodiment, a water-soluble drug for use with an ME is pregabalin.

In another aspect are provided methods for treating glaucoma or reducing IOP, comprising administering to a subject in need thereof an amount effective to treat glaucoma or reduce IOP of an inhibitor of Calcium Voltage-Gated Channel Auxiliary Subunit Alpha2Delta1 (CACNA2D1) protein. In one embodiment, the methods are to treat glaucoma; in one such embodiment, the glaucoma is primary open angle glaucoma (POAG). In one embodiment, the inhibitor comprises a gabapentanoid, phenylglycine, or a pharmaceutically acceptable salt thereof. In another embodiment, the gabapentanoid comprises pregabalin, or a pharmaceutically acceptable salt thereof.

As used herein, the phrase "pharmaceutically acceptable salt" refers to both pharmaceutically acceptable acid and base addition salts and solvates. Such pharmaceutically acceptable salts may be any salts suitable for san intended use, including but not limited to salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like.

Non-toxic pharmaceutical base addition salts include salts of bases such as sodium, potassium, calcium, ammonium, and the like. Those skilled in the art will recognize a wide variety of non-toxic pharmaceutically acceptable addition salts.

As used here, a subject "in need thereof" refers to a subject that has the disorder or disease to be treated or is predisposed to or otherwise at risk of developing the disease or disorder.

In one non-limiting example, the MEs may comprise or consist of the following components:
(a) a primary water-in-oil (w/o) phase constituting between about 0.1% and about 40% of the formulation, wherein the w/o phase comprises:
 (i) water at a concentration of between 0% and about 7% w/w of the formulation;
 (ii) oil at a concentration of between about 6% and about 13% w/w of the formulation;
 (iii) Capryol®90 (propylene glycol monoester of caprylic acid) at a concentration of between about 1% and about 13% w/w of the formulation; and
 (iv) lecithin at a concentration of between about 1% and about 13% w/w of the formulation; and
(b) an external aqueous phase constituting 50-99.9% of the formulation, wherein the external aqueous phase comprises:
 (i) labrasol at a concentration of between about 0.1% and about 25% w/w of the formulation;
 (ii) cremophor EL at a concentration of between about 0.1% and about 25% w/w of the formulation;
 (iii) propylene glycol at a concentration of between 0% and about 45% w/w of the formulation; and
 (iv) water at a concentration of between about 10% and about 99.7% w/w of the formulation.

In another non-limiting example, the MEs may comprise or consist of the following components:
(a) a primary water-in-oil (w/o) phase constituting between about 0.1% and about 40% of the formulation, wherein the w/o phase comprises:
 (i) water at a concentration of between 2% and about 7% w/w of the formulation;
 (ii) oil at a concentration of between about 6% and about 9% w/w of the formulation;
 (iii) Capryol® 90 (propylene glycol monoester of caprylic acid) at a concentration of between about 3% and about 9% w/w of the formulation; and
 (iv) lecithin at a concentration of between about 3% and about 9% w/w of the formulation; and
(b) an external aqueous phase constituting 50-99.9% of the formulation, wherein the external aqueous phase comprises:
 (i) labrasol at a concentration of between about 5% and about 9.5% w/w of the formulation;
 (ii) Cremophor EL at a concentration of between about 5% and about 9.5% w/w of the formulation;
 (iii) propylene glycol at a concentration of between 5% and about 25% w/w of the formulation; and
 (iv) water at a concentration of between about 30% and about 56% w/w of the formulation.

In another aspect are provided microemulsions designed as a drug delivery system for water-insoluble and sparingly-water soluble drugs molecules. In these embodiments, the MEs are the same as described above, but lack the internal aqueous phase and internal emulsifier. Thus, in this embodiment the ME comprises:
(a) a discontinuous (dispersed) oil phase; and
(b) an emulsifier encompassing the oil phase.

In one embodiment, the ME further comprises (c) a continuous aqueous phase surrounding the emulsifier. In this embodiment, the oily drug solution is emulsified in the bioadhesive aqueous phase (such as a hydrogel as described herein) that contains a hydrophilic emulsifier (i.e. emulsifier with high HLB value).

In a further embodiment, the ME comprises an insoluble or sparingly soluble drug in the discontinuous oil phase.

All embodiments disclosed above for the MEs can be used in this aspect as well, unless the context clearly dictates otherwise.

Examples

Cacna2d1 is Identified as an IOP-Modulating Gene

We systematically measured IOP across a large subset of the BXD family in multiple age cohorts. Using stringent stepwise refinement based on expression quantitative trait locus (QTL) mapping, correlation analyses (direct and partial Pearson test), and the analysis of single-nucleotide polymorphisms (SNPs), we are able to identify a candidate gene that modulates IOP, and using mouse and human genetic data, we can validate the candidate gene. To determine the candidate gene variants that modulate IOP within the Chr 5 locus, we used the following stringent criteria): (1) the gene is located within the confidence interval of the peak eQTL; (2) the gene has cis-modulation; (3) the expression level of the gene across BXD strains is significantly correlated with elevated IOP using both linear correlation and partial Pearson correlation analyses; (4) the gene functions within a network that could explain its role in modulating IOP; (5) the gene has sequence variants between parental strains at/near the region of the gene; (6) the gene is expressed in the eye and localized to an area associated with modulation of IOP; (7) the gene is associated with human POAG and/or elevated IOP either through GWAS or standard linkage studies; and (8) the gene has a biological association with glaucoma or its treatment. Within the QTL peak at Chr 5, there were 25 positional gene candidates that were cis-regulated. Using our above criteria, calcium channel, voltage-dependent, a2δ1 subunit (Cacna2d1) emerged as the single best positional candidate (r=0.440; P=0.0003) (FIG. 1).

Figure 2:
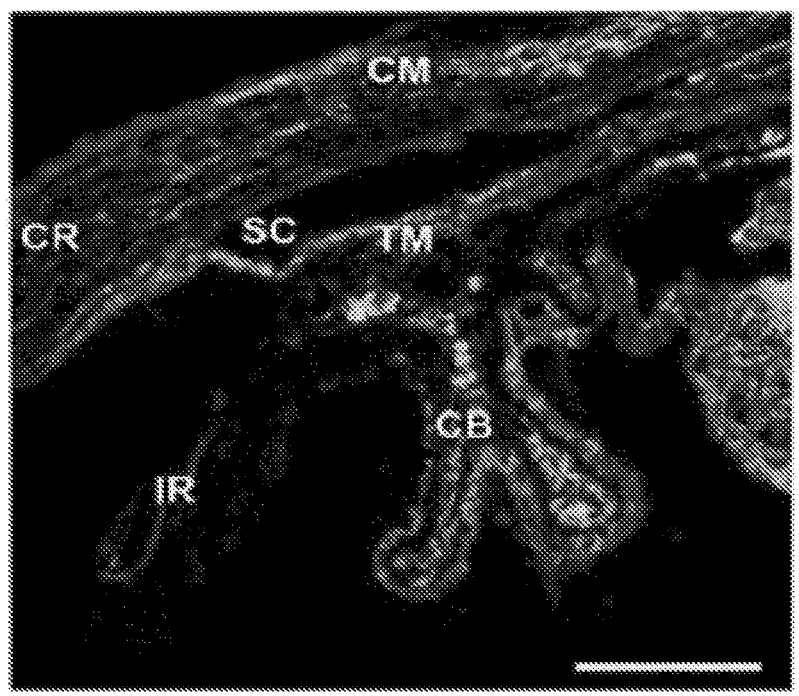
FIG. 2: CACNA2D1 is localized to the ciliary body (CB) & trabecular meshwork (TM).

To further test Cacna2d1 as a candidate IOP modulating gene, we performed immunohistochemistry to determine the localization pattern of CACNA2D1 in healthy mouse and human donor eyes. In the mouse eye, CACNA2D1 is prominently localized to the TM, CB, and ciliary muscle (CM). CACNA2D1 was observed in a punctate pattern throughout the TM and Schlemm's canal. In the CB, CACNA2D1 was highly expressed in the non-pigmented epithelium. Weak labeling was present in the CM (FIG. 2).

Figure 3:
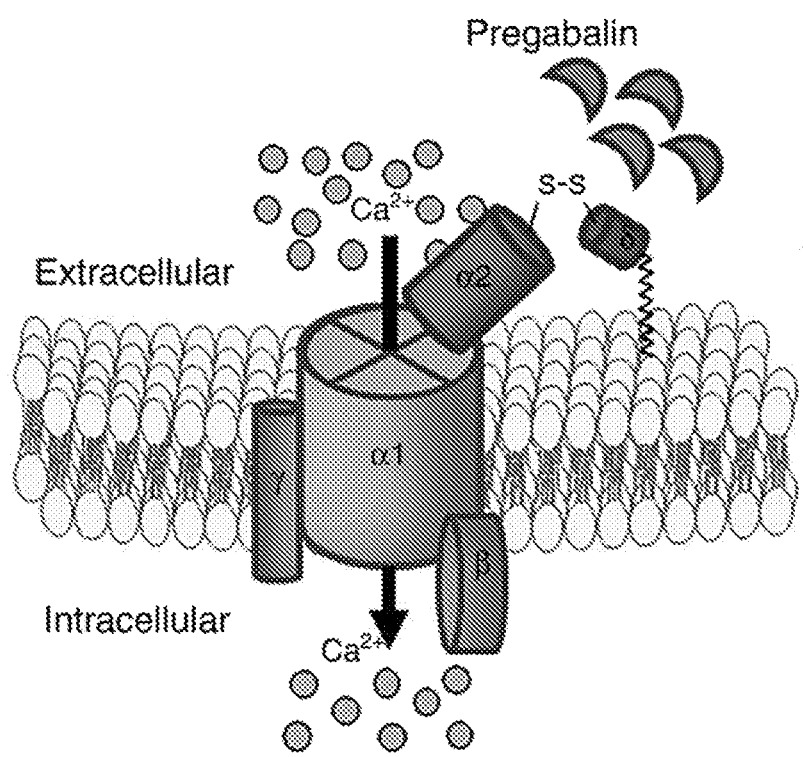
FIG. 3: Cartoon showing association of CACNA2D1 with the Caval pore and binding of pregabalin to the CACNA2D1 subunit.
Figure 4:
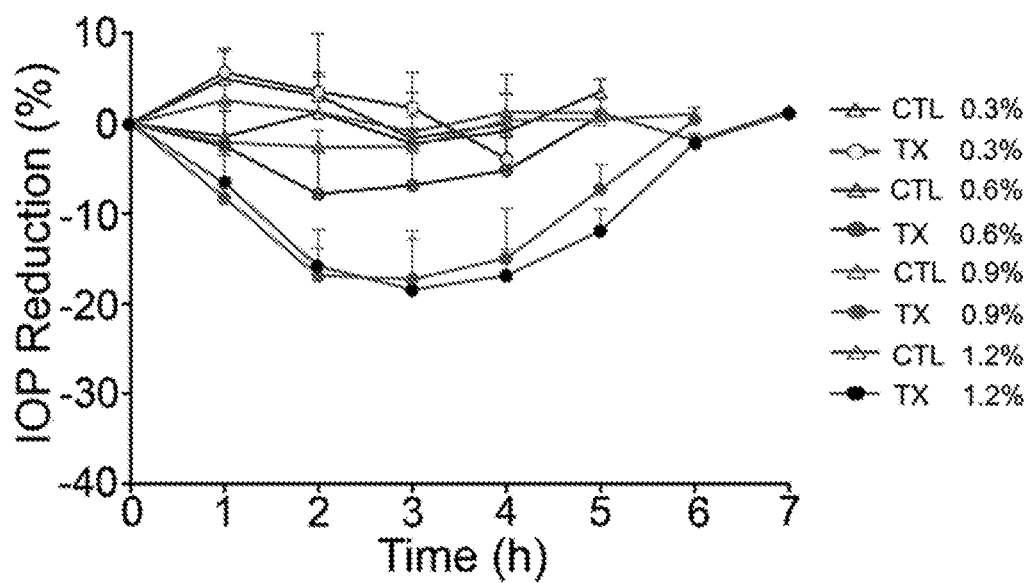
FIG. 4: Pregabalin suspended in hydroxypropyl methylcellulose (HPMC) lowers IOP in B6 mice in a dose-dependent manner. 0.9% is the minimum concentration that gives maximum effect (n=5).
Figure 5:
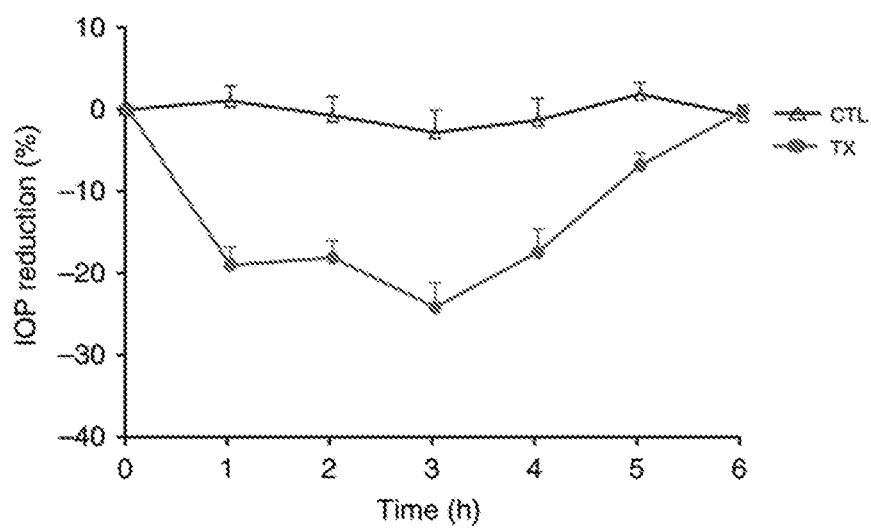
FIG. 5: Pregabalin (0.9%) suspended in hydroxypropyl methylcellulose (HPMC) lowers IOP by 23% in Dutch belted rabbits (n=5).
Figure 6:
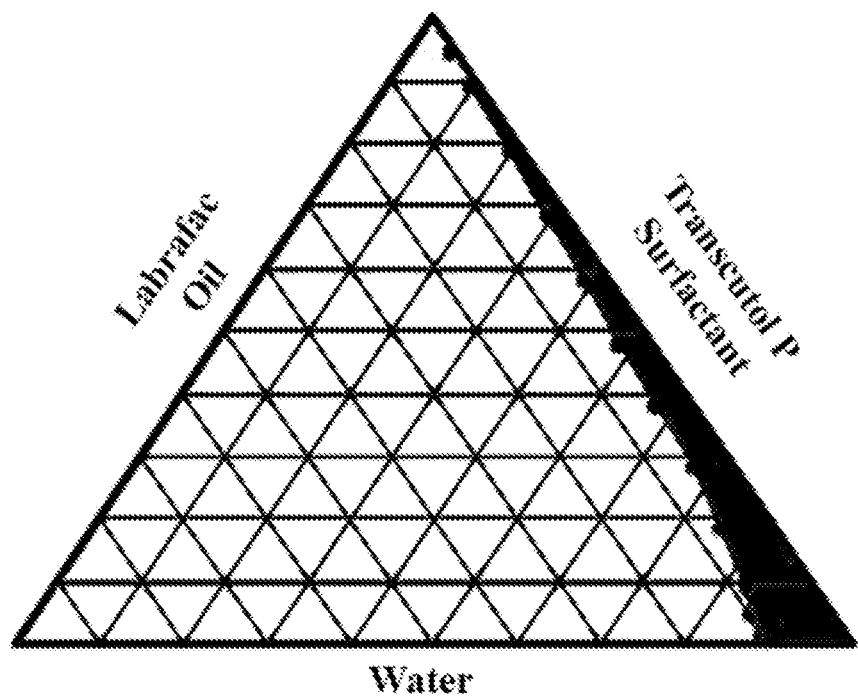
FIG. 6: Triphase diagram of Labrafac™ (medium chain triglyceride of caprylic ($C_8$) and capric ($C_{10}$) acids) (oil)+Transcutol® P (diethylene glycol monoethyl ether) (surfactant)+$H_2O$, w/o microemulsion is shown in the shaded region.
Figure 7:
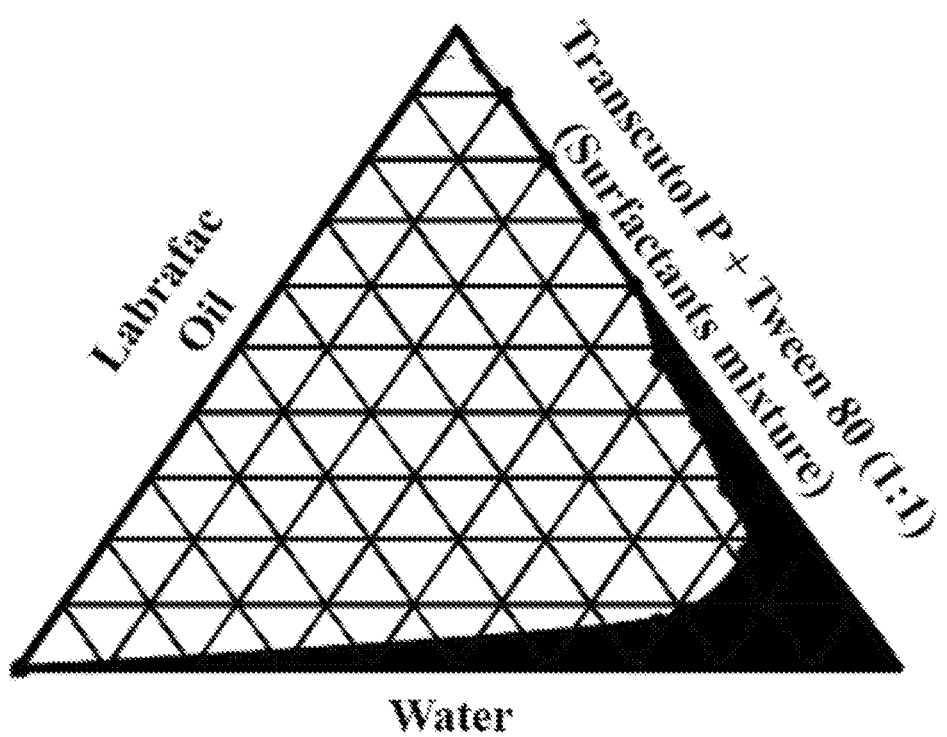
FIG. 7: Pseudotriphase diagram of Labrafac™ (medium chain triglyceride of caprylic ($C_8$) and capric ($C_{10}$) acids) (oil)+Transcutol® P (diethylene glycol monoethyl ether) & tween80 (surfactant mixture)+$H_2O$, w/o microemulsion is shown in the shaded region.
Figure 8:
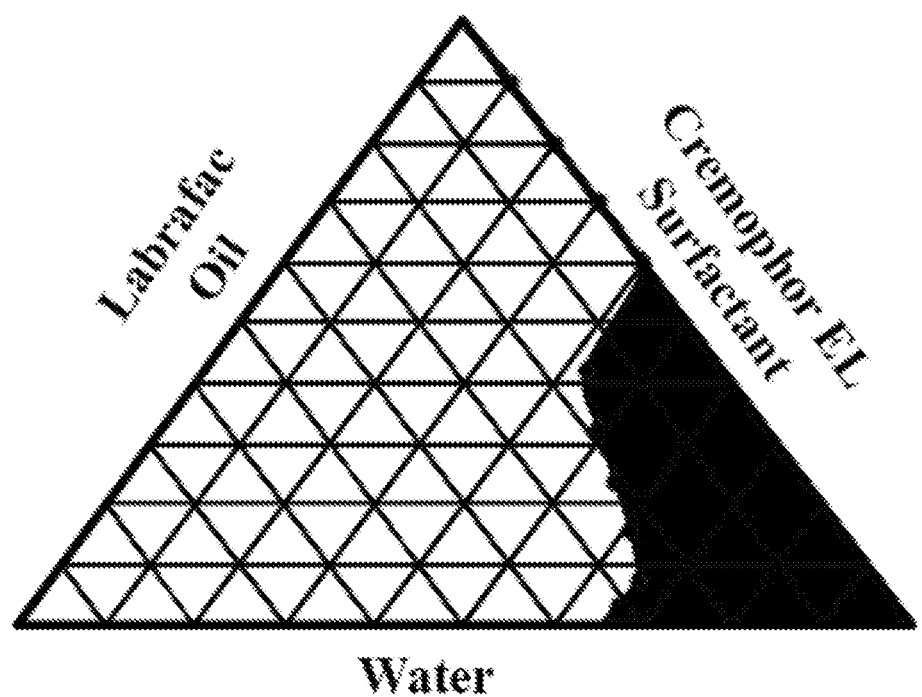
FIG. 8: Triphase diagram of Labrafac™ (medium chain triglyceride of caprylic ($C_8$) and capric ($C_{10}$) acids) (oil)+cremophor EL (surfactant)+$H_2O$, w/o microemulsion is shown in the shaded region.
Figure 9:
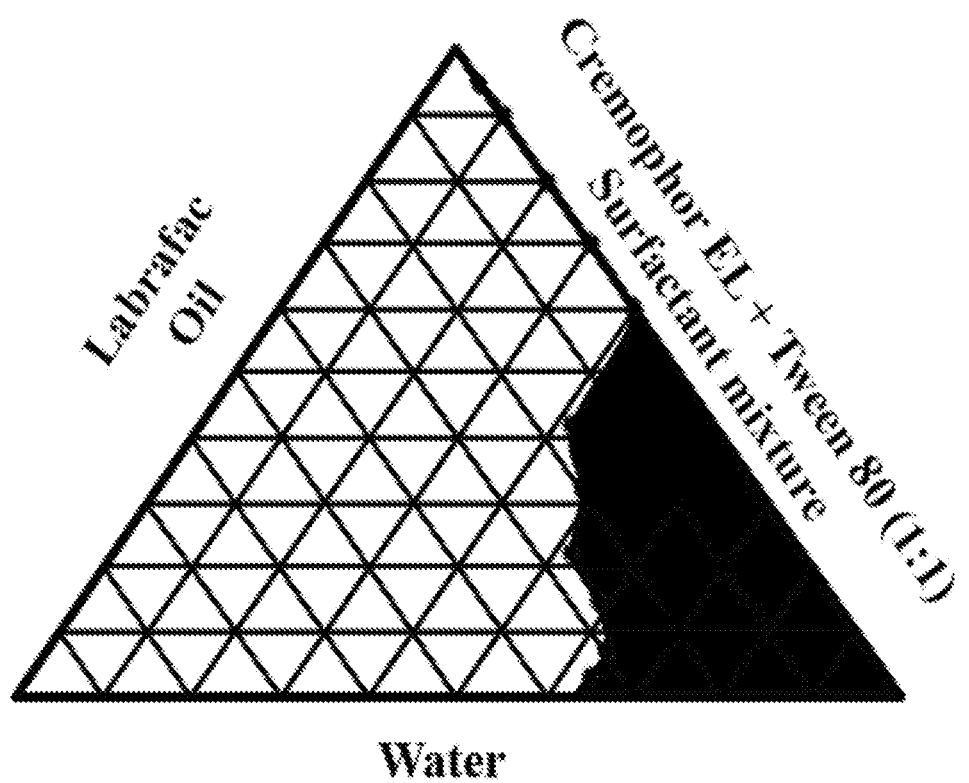
FIG. 9: Pseudotriphase diagram of Labrafac™ (medium chain triglyceride of caprylic ($C_8$) and capric ($C_{10}$) acids) (oil)+cremophor EL & tween 80 (surfactant mixture)+$H_2O$, w/o microemulsion is shown in the shaded region.
Figure 10:
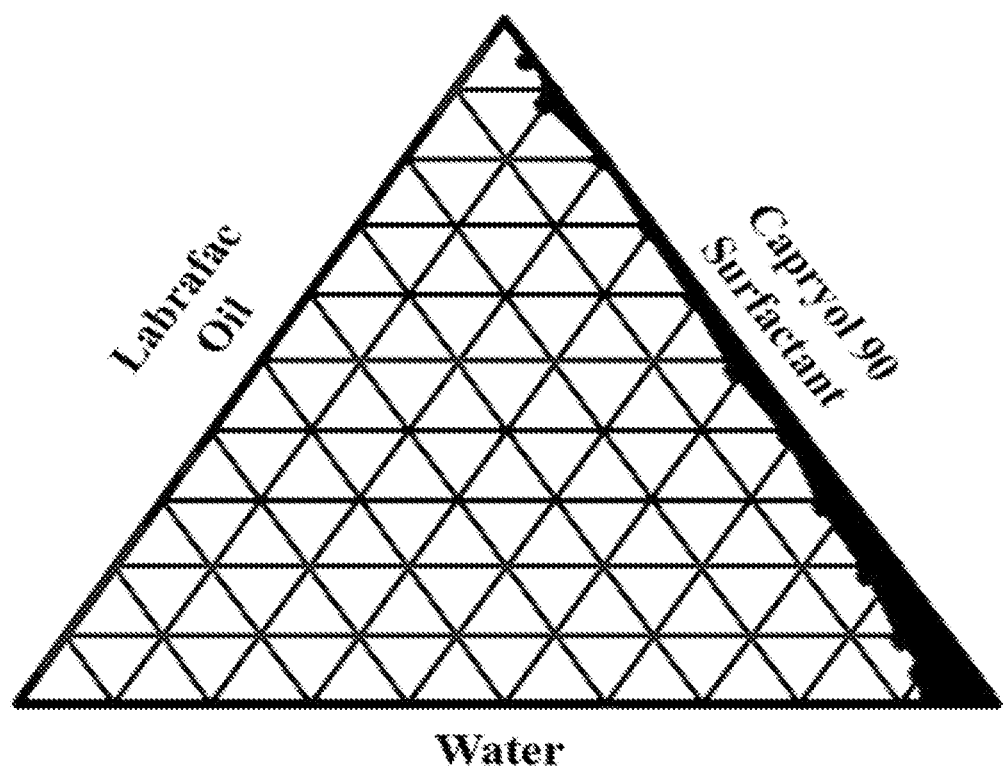
FIG. 10: Triphase diagram of Labrafac™ (medium chain triglyceride of caprylic ($C_8$) and capric ($C_{10}$) acids) (oil)+Capryol® 90 (propylene glycol monoester of caprylic acid) (surfactant)+$H_2O$, w/o microemulsion is shown in the shaded region.
Figure 11:
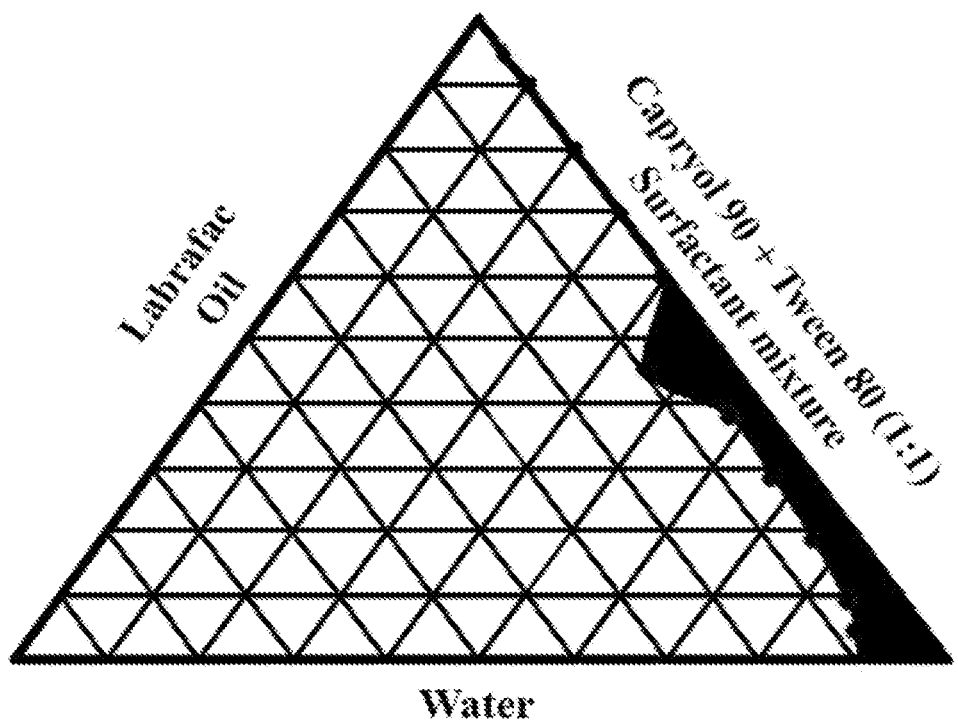
FIG. 11: Pseudotriphase diagram of Labrafac™ (medium chain triglyceride of caprylic ($C_8$) and capric ($C_{10}$) acids) (oil)+Capryol® 90 (propylene glycol monoester of caprylic acid) & tween 80 (surfactant mixture)+$H_2O$, w/o microemulsion is shown in the shaded region.
Figure 12:
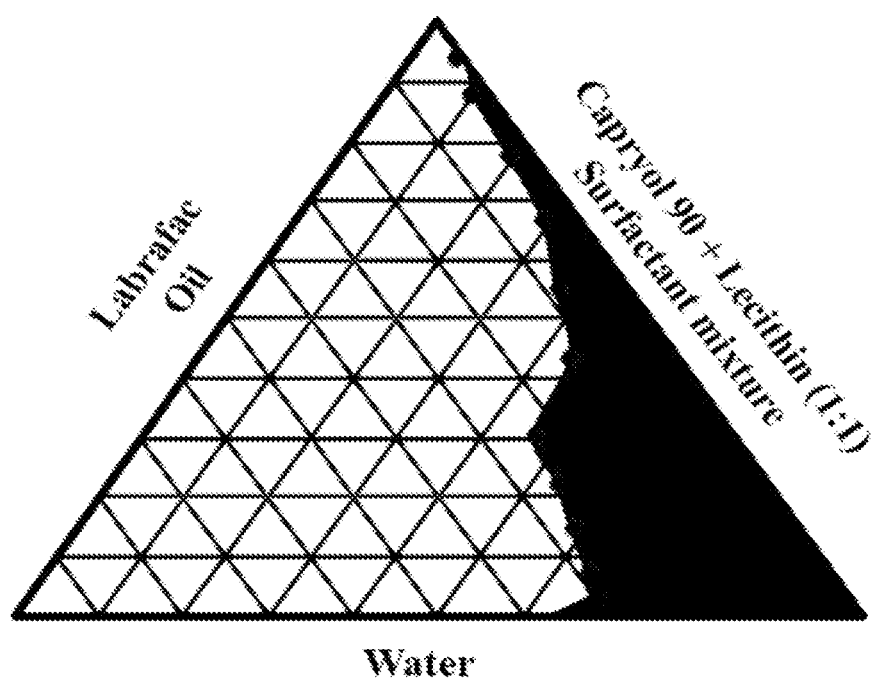
FIG. 12: Pseudotriphase diagram of Labrafac™ (medium chain triglyceride of caprylic ($C_8$) and capric ($C_{10}$) acids) (oil)+Capryol®90 (propylene glycol monoester of caprylic acid) & soybean lecithin (1:1) (surfactant mixture)+$H_2O$, w/o microemulsion is shown in the shaded region.
Figure 13:
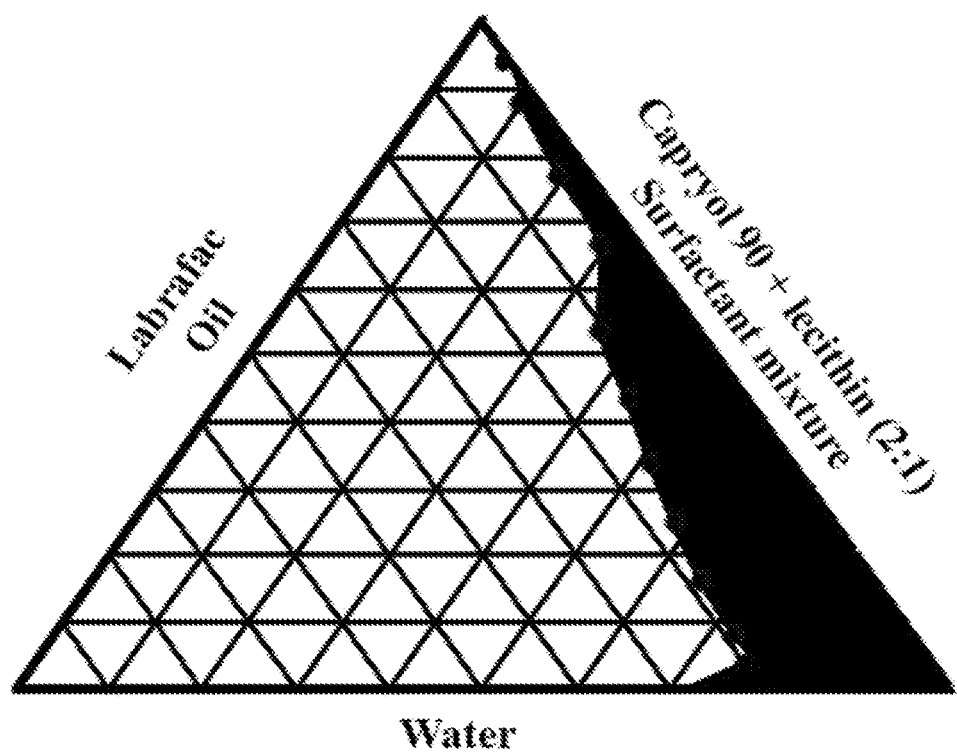
FIG. 13: Pseudotriphase diagram of Labrafac™ (medium chain triglyceride of caprylic ($C_8$) and capric ($C_{10}$) acids) (oil)+Capryol® 90 (propylene glycol monoester of caprylic acid) & soybean lecithin (2:1) (surfactant mixture)+$H_2O$, w/o microemulsion is shown in the shaded region.

We showed that CACNA2D1 is expressed in both CB and TM. It is also modestly present in the CM. Based upon these collective data, it appears that CACNA2D1 regulates IOP (FIG. 3). Pregabalin, or other gabapentinoid drugs, binds to the CACNA2D1 subunit of the calcium channel. The binding of the drug mitigates the flux of calcium through the α1 pore of the calcium channel, reducing the level of intracellular calcium. Since Cacna2d1 modulates IOP, pregabalin, a gabapentinoid drug with high specificity for CACNA2D1, was evaluated for its ability to affect IOP. Pregabalin ophthalmic eye drops [(pregabalin suspended in hydroxypropyl methylcellulose (HPMC)] reduce IOP in mice in a dose-dependent manner from 0.3-1.2% (FIG. 4). Drops containing 0.3% drug provided no IOP-lowering effect compared to control. All other concentrations of drug reduced IOP in a dose-dependent manner. A plateau was reached at 0.9% and there was no significant difference in drug response between 0.9 and 1.2% drug (P>0.05). There was no significant difference between the time of maximum response ($T_{max}$) values of 0.6-1.2% concentrations of drug (P>0.05). In contrast, there was a significant difference between the time required for IOP to return to baseline ($T_{end}$) for all concentrations of pregabalin eye drops, (P<0.0001). The 1.2% pregabalin eye drops extended the duration of the IOP-lowering effect of pregabalin above that obtained with 0.6% pregabalin. Because there was no significant difference in the percent reduction of IOP between 0.9 and 1.2% pregabalin, we selected 0.9% as the minimal concentration required to produce the maximum reduction in IOP. Expanding this analysis to an additional species, we observed a similar IOP-lowering response (22.1±2.8%) in Dutch belted rabbits after instillation of 0.9% pregabalin eye drops (FIG. 5).

Extended Release Pregabalin Microemulsion formulation as a Novel Glaucoma Therapy Primary open angle glaucoma (POAG) accounts for 90% of glaucoma cases worldwide. It is a leading cause for irreversible blindness. Elevated intraocular pressure (IOP) is the most significant risk factor that contributes to visual field loss in POAG. IOP is generated by the balance between the production and drainage of aqueous humor. Because of the importance of a tightly maintained IOP, its reduction is the first-line treatment for glaucoma. Despite glaucoma prevalence and its impact on society, current medications do not address the underlying pathophysiologies that cause elevated IOP, nor do they address genetic variations related to IOP modulation. Moreover, because of their short half-life and low corneal residence time, they require multiple daily topical applications, which are associated with poor patient compliance. We have developed novel extended release topical bioadhesive microemulsion (ME) formulations to deliver pregabalin (an exemplary IOP-lowering drug) that will allow for once daily dosing and better patient compliance.

Formulation of Pregabalin-Loaded Bioadhesive Multilayered ME

Formulation of the bioadhesive multilayered ME hydrogel was achieved in three steps. The first step included formation of the primary water-in-oil (w/o) ME through construction of different triphase diagrams. The second step involved further emulsification of the produced primary w/o ME into hydrophilic surfactant aqueous solution (i.e. surfactant with high value of hydrophilic lipophilic balance, HLB). The last step included the incorporation of the bioadhesive polymer.

Construction of Triphase Diagrams and Preparation of the Primary w/o ME

The primary w/o ME usually consists of an oil phase, aqueous phase, single surfactant or surfactants mixture. To determine the appropriate ratio of each component that can efficiently produce a ME, multiple triphase and pseudotriphase diagrams were constructed using Labrafac™ lipophile WL1349 (medium chain triglyceride of caprylic ($C_8$) and capric ($C_{10}$) acids) as the oil phase, deionized water as the aqueous phase and a single surfactant (in case of triphase diagram) or surfactant mixture (in case of pseudotriphase diagram) from the following surfactants: Capryol 90 (propylene glycol monoester of caprylic acid); labrasol, cremophor EL; Transcutol® P (diethylene glycol monoethyl ether); Gelucire® 50/13 (mixture of PEG (MW 1500) mono-, di-, tri-esters of stearic acid); Gelucire® 44/14 (mixture of PEG (MW 1500) mono-, di-, tri-esters of lauric acid); Gelucire® 43/01 (mixture of PEG (MW 1500) mono-, di-, tri-esters of fatty acids $C_8$-$C_{18}$); or soybean lecithin.

Figure 14:
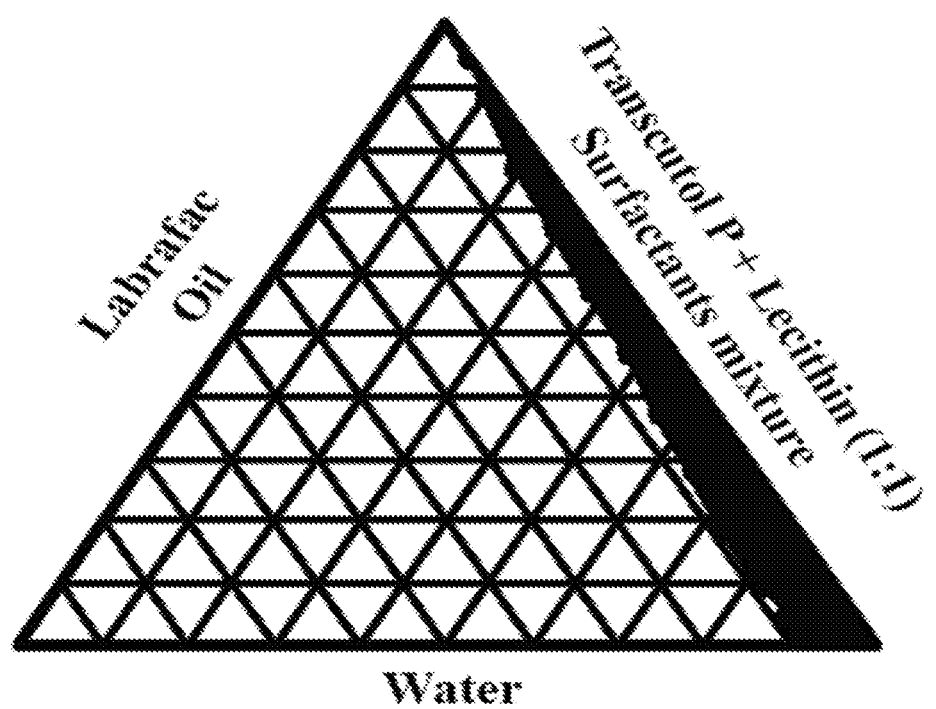
FIG. 14: Pseudotriphase diagram of Labrafac™ (medium chain triglyceride of caprylic ($C_8$) and capric ($C_{10}$) acids) (oil)+Transcutol® P (diethylene glycol monoethyl ether) & soybean lecithin (1:1) (surfactant mixture)+$H_2O$, w/o microemulsion is shown in the shaded region.
Figure 16:
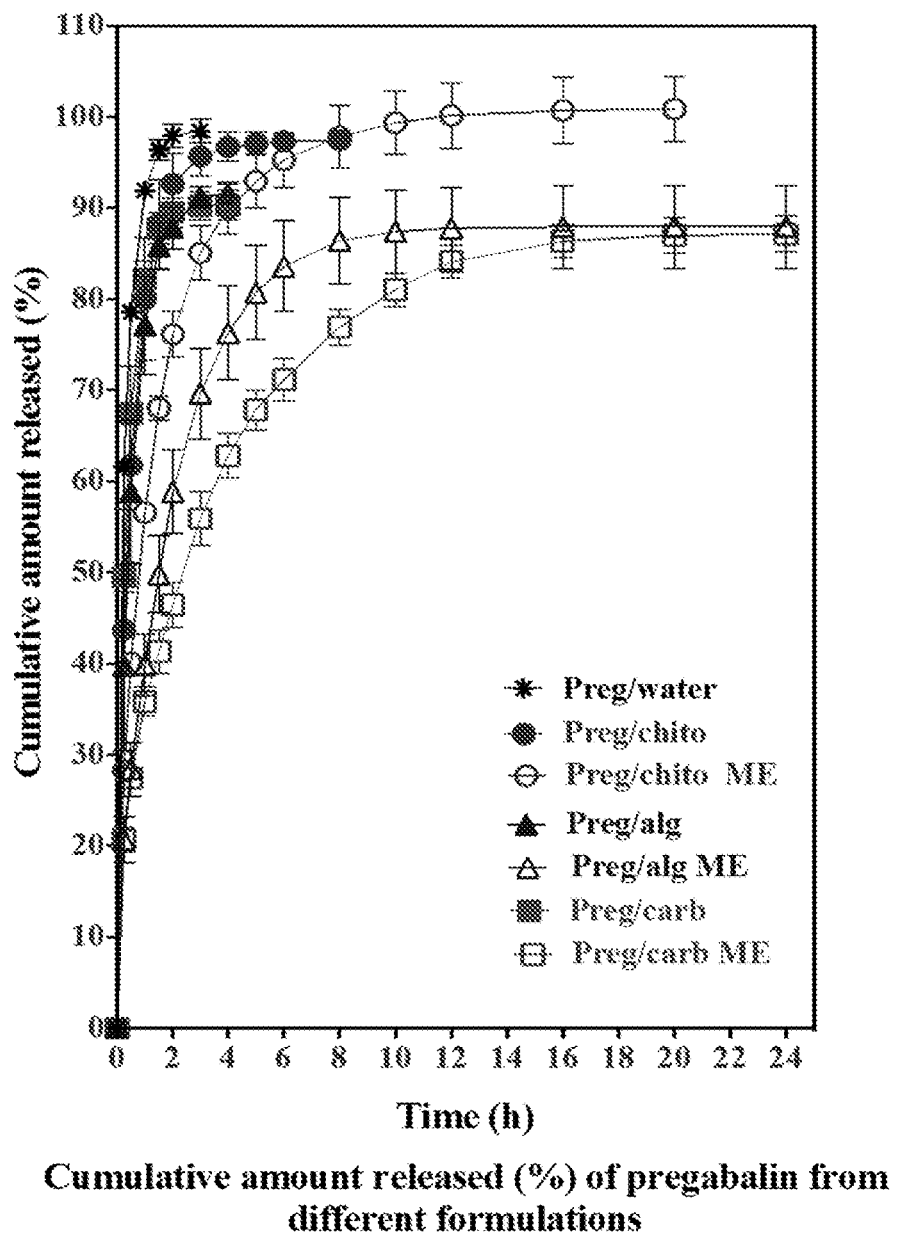
FIG. 16: Pregabalin release profiles from different formulations show the sustained release behavior of MEs, which is especially clear in CARBOPOL® (carbomer) ME, that gave a steady release rate that lasted for up to 24 h.

The triphase diagrams (FIG. 6-14) were generated using a water titration method. In this method, oil was mixed with surfactant or surfactants mixture in different ratios. The produced mixture was then titrated with deionized water until the appearance of the first turbidity, which reflects the boundary point that differentiates the end of the w/o ME region and the beginning of the microemulsion region. In FIG. 16-14, the w/o ME region is shaded in black color and illustrate all the possible combinations of the three components that are capable of forming a ME. By selecting any point in that region, one can determine the percentage of the three components that can be easily mixed to form a w/o ME.

Preparation of the Multilayered w/o/w ME

Several triphase diagrams were constructed. The diagram represented in FIG. 12 was selected because it has the largest ME region. One point was selected (though others would have worked as well) from this diagram to be used for formulation of the multilayered water-in-oil-in-water (w/o/w) ME. All triphase diagrams were constructed using percent ratio of each ingredient (water, surfactant/surfactant mixture and oil) from 0-100%. The selected w/o ME consisted of 20% water+30% oil (Labrafac™ lipophile WL1349 (medium chain triglyceride of caprylic ($C_8$) and capric ($C_{10}$) acids))+50% surfactant mixture (Capryol® 90 (propylene glycol monoester of caprylic acid) & soybean lecithin, 1:1). The selection of this point was based on obtaining a stable w/o primary emulsion with the highest possible amount of water in its internal phase that is capable of dissolving the drug in the required dose. The selected concentration of the drug is 0.6%. To prepare the final multilayered w/o/w ME, several surfactants with high HLB were screened to determine those that work well in the formulation of the multilayered w/o/w ME using titration method. The tested surfactants were cremophor EL, labrasol, tween 80, poloxamer 188 and brij 97. These surfactants may be used alone or in combination with each other or with other co-solvents such as polyethylene glycol, propylene glycol or glycerin. Aqueous solutions of different concentrations of these surfactants were prepared. The previously selected w/o was added drop wise to these solutions under continuous stirring until the appearance of the first turbidity, which indicated the end of the ME formation and the beginning of the macroemulsion formation. Among these surfactants, labrasol was not used at a concentration above 10% as it could result in irritation to the rabbits' eyes. Labrasol was used in combination with other surfactants (10% labrasol+10% cremophor EL+30% propylene glycol). By using this combination, the amount of w/o ME incorporated was 3.7 gm. The selected surfactant system is highlighted in Table 1.

TABLE 1

Different surfactant systems evaluated.

| Number | Surfactant | Concentration | Amount of w/o ME (gm) |
|---|---|---|---|
| 1 | Water | — | 0.01 |
| 2 | tween 80 | 2.5% | 0.02 |
| 3 | tween 80 | 5% | 0.05 |
| 4 | tween 80 | 10% | 0.05 |
| 5 | cremophor EL | 10% | 0.02 |
| 6 | poloxamer 188 | 10% | 0.02 |
| 7 | brij 97 | 10% | 0.02 |
| 8 | labrasol | 10% | 1 |
| 9 | labrasol | 20% | 1.6 |
| 10 | labrasol | 30% | 2.5 |
| 11 | labrasol | 40% | 3.2 |
| 12 | propylene glycol | 40% | 0.1 |
| 13 | labrasol 20% + propylene glycol 10% | | 2 |
| 14 | labrasol 30% + propylene glycol 10% | | 4 |
| 15 | labrasol 20% + propylene glycol 20% | | 3.25 |
| 16 | labrasol 10% + propylene glycol 30% | | 1.55 |
| 17 | labrasol 10% + propylene glycol 10% + tween-80 10% | | 1.2 |
| 18 | labrasol 10% + propylene glycol 10% + brig-97 10% | | 1.2 |
| 19 | labrasol 10% + propylene glycol 10% + cremophor-EL 10% | | 1.65 |
| 20 | labrasol 10% + propylene glycol 20% + cremophor-EL 10% | | 2.1 |
| 21 | Labrasol 10% + propylene glycol 30% + cremophor EL 10% | | 3.7 |
| 22 | labrasol 5% + propylene glycol 30% + cremophor-EL 10% | | 2.5 |

Formulation of the Final Bioadhesive Multilayered ME Hydrogel

Figure 15:
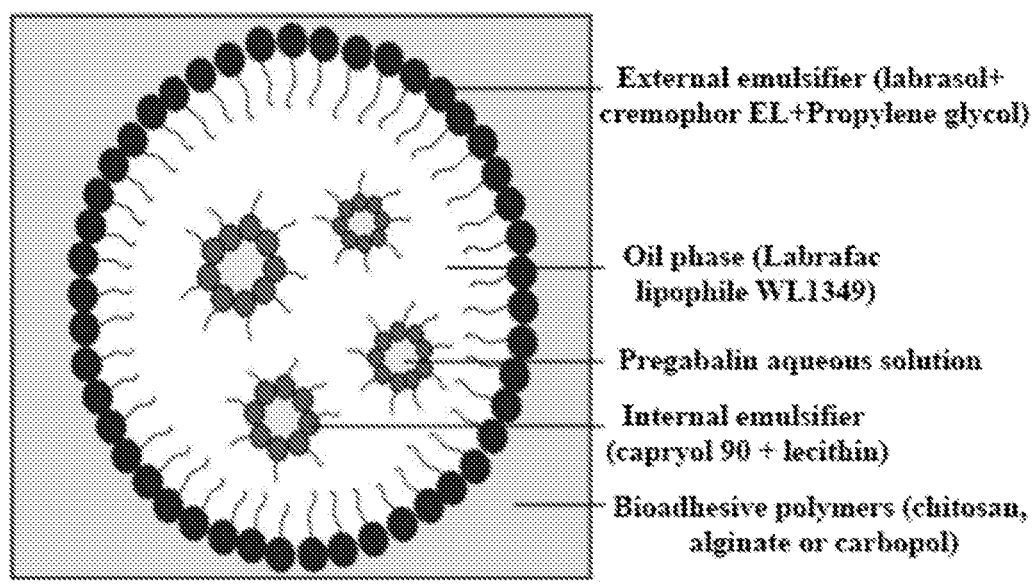
FIG. 15: Cartoon showing composition of multilayered ME hydrogel.

The external aqueous phase was prepared by dissolving 10% labrasol, 10% cremophor EL and 30% propylene glycol in distilled water. The bioadhesive polymer (CARBOPOL® 981 (carbomer homopolymer type A (allyl pentaerythritol crosslinked), sodium alginate or chitosan) was soaked in the previously prepared surfactants solution and allowed to swell overnight. The previously prepared primary drug-loaded w/o is incorporated drop wise in this viscous polymer solution until gave the final clear multilayered w/o/w ME hydrogel (FIG. 15). Table 2 lists the chemical compositions of the three ME formulations we tested.

TABLE 2

Composition of pregabalin-loaded ME

| Ingredient (% W/W) | Chitosan ME | Sod. alginate ME | CARBOPOL ® ME |
|---|---|---|---|
| Pregabalin | 0.6 | 0.6 | 0.6 |
| Labrafac ™ lipophile WL1349 (medium chain triglyceride of caprylic ($C_8$) and capric ($C_{10}$) acids) | 7.8 | 7.8 | 7.8 |
| Capryol ® 90 (propylene gylcol monoester of caprylic acid) | 6.5 | 6.5 | 6.5 |
| Lecithin | 6.5 | 6.5 | 6.5 |
| labrasol | 7.4 | 7.4 | 7.4 |
| Cremophor EL | 7.4 | 7.4 | 7.4 |
| Propylene glycol | 22.2 | 22.2 | 22.2 |
| Chitosan | 1.1 | — | — |
| Sod. alginate | — | 0.4 | — |
| CARBOPOL ® 981 (carbomer homopolymer type A (allyl pentaerythritol cross-linked) | — | — | 0.15 |
| Deionized water to | 100 | 100 | 100 |

Characterization of the Prepared Multilayered Pregabalin ME Hydrogels
In Vitro Characterizations In vitro characterizations of the pregabalin ME hydrogel included: drug release study, cell toxicity study, viscosity determination, mucoadhesion study, and particle size and zeta potential determination.

Drug Release Study

The sustained release behaviors of pregabalin from different formulations were studied in PBS (pH 7.4) using 1500 µl fast micro-equilibrium dialyzer (Harvard Apparatus Co., Holliston, MA) with semipermeable regenerated cellulose membranes (Molecular weight cut off 5,000 Da). The dialyzers were kept in a thermostatically controlled shaker at 35° C. and 50 rpm. Samples were withdrawn at predetermined time intervals for 24 h and analyzed for their drug content by HPLC. The tested formulations were CARBOPOL® (carbomer), alginate, and chitosan MEs that contained 0.6% pregabalin in addition to 4 control formulations including; CARBOPOL® (carbomer), alginate, chitosan and water that contained 0.6% pregabalin. The release profiles (FIG. 16) show that all control formulations exhibited fast release behaviors that released 100% of the drug content within 3-8 h. On the other hand, the tested MEs exhibited sustained release behaviors that last for up to 24 h.

Cell Toxicity Study

In-vitro cell toxicity of the ophthalmic formulations was tested using an MTT assay method according to known protocols. Briefly, immortalized human corneal limbal epithelial cell (HCLE) were seeded in 96-well plate (18,000 cell/well) with 200 µl growth medium and kept overnight at (37° C. & 5% $CO_2$) without disturbance to allow it to attach itself to the well bottom. In the next day the medium was removed and replaced with 200 µl of the formulation solution in the growth medium. The formulations were kept in contact with the cells for 24 h then replaced by 200 µl of (1 mg/ml) MTT solution. The plate was kept at (37° C. & 5%

$CO_2$) for 4 h to allow the cells to reduce MTT to the purple formazan crystals. After 4 h, MTT solution was replaced by 200 μl DMSO to dissolve the formazan crystals. The plate UV absorbance was measured at 570 nm using microplate reader spectrophotometer. The cell viability for the tested formulations was calculated using their absorbance values as a percentage of the negative control (untreated cells) absorbance according to the following equation;

$$\% \text{ Cell viability} = \frac{\text{Sample absorbance}}{\text{Negative control absorbance}} \times 100$$

Figure 17:
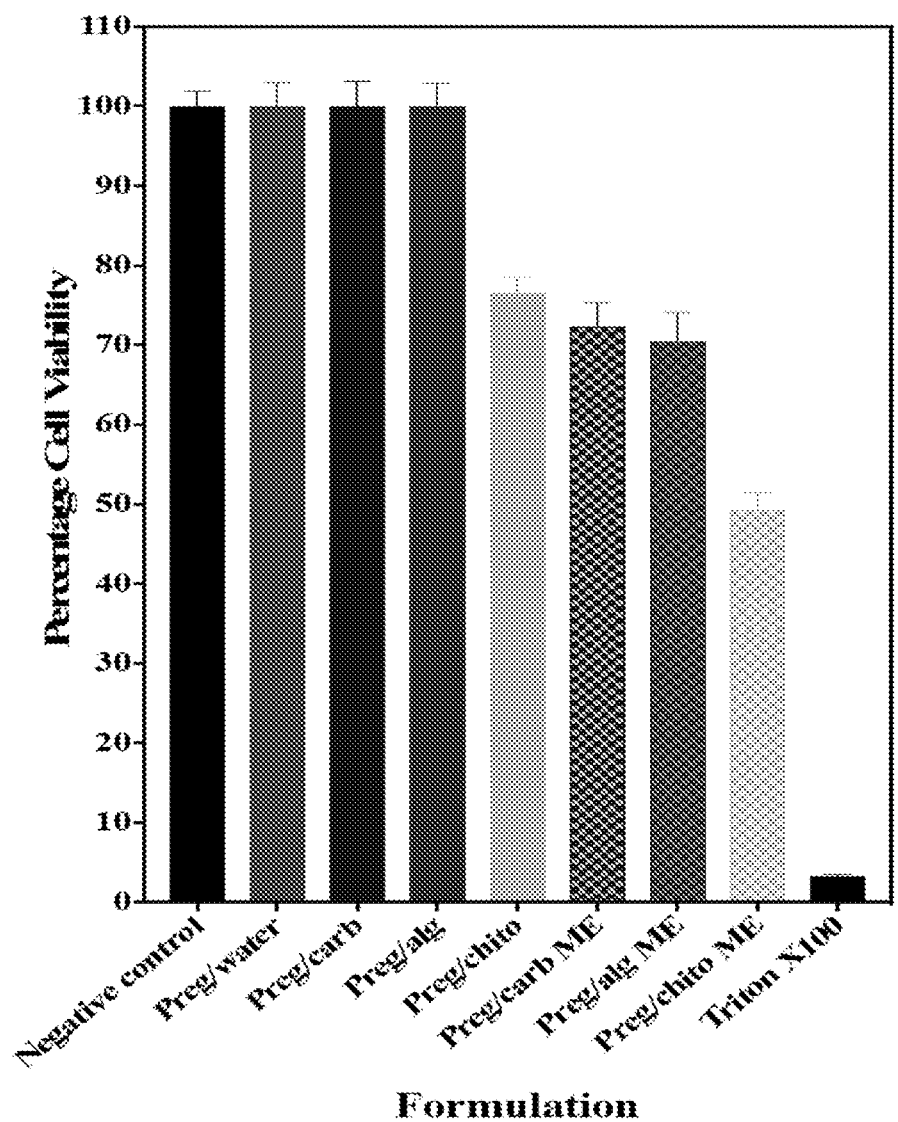
FIG. 17: Histograms of cytotoxicity pattern of different pregabalin formulations containing pregabalin show the safety of the formulations to human corneal epithelial cells.

FIG. 17 shows that the formulations are safe and nontoxic for the corneal epithelial cells at the therapeutic dose. The experiment was repeated 8 times for each formulation and the results were calculated as mean±SEM.

Viscosity Study

Figure 18:
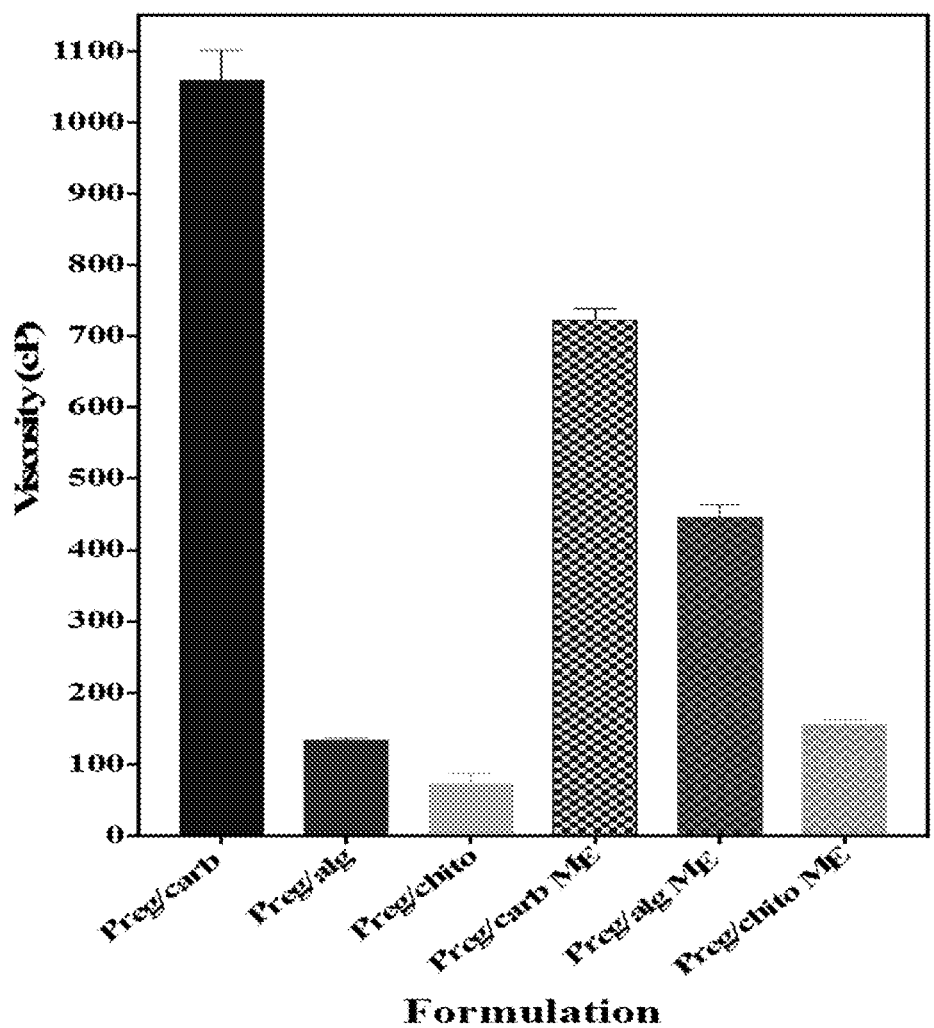
FIG. 18: Histograms of pregabalin formulation viscosity show that the formulation containing CARBOPOL® (carbomer) possesses the highest viscosity value, which allow it to remain on the eye for longer time.

Viscosity of the formulations was measured using Brookfield cone and plate rotary viscometer according to a previously published protocol. Five hundred microliters of each formulation were placed between the cone and plate and allowed to equilibrate for 1 min to reach the running temperature. The measurements were done at 35° C.±0.5. The experiment was repeated three times and the results were calculated as mean±SEM. FIG. 18 shows that the formulations containing CARBOPOL® (carbomer) possessed the highest viscosity value, which allow them to remain inside the eye for longer time. This improved corneal contact time will prolong the IOP lowering effect and help the sustained release of the drug.

Where: $\eta_b = \eta_t - (\eta_m + \eta_r)$
$\eta_b$: change in viscosity (rheological synergism) (cP)
$\eta_t$: viscosity of the mixture (cP)
$\eta_m$: viscosity of mucin (cP)

$F = \eta_b \cdot \gamma$
$\eta_r$: viscosity of the formulation (cP)
F: mucoadhesion force (dyne/cm$^2$)
γ: shear rate (S$^{-1}$)

Figure 19:
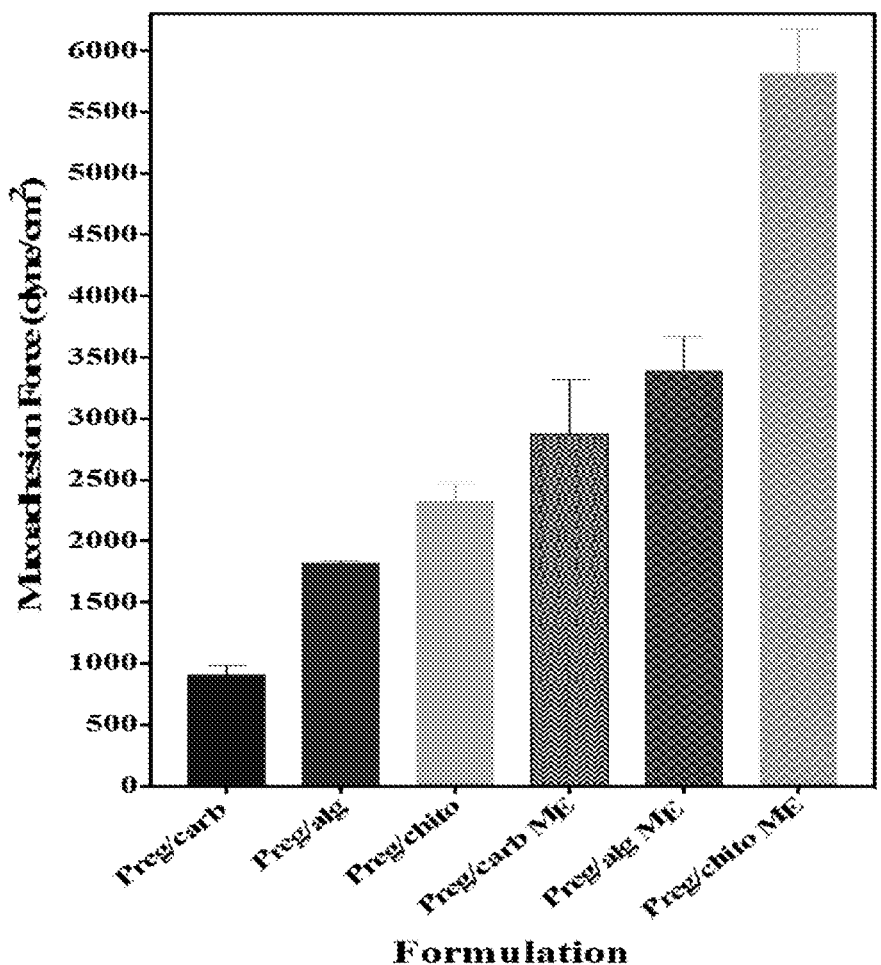
FIG. 19: Histograms of pregabalin formulation mucoadhesion show that the ME formulations possess higher mucoadhesion value than the other formulations.

The experiment was repeated three times and the results were calculated as mean±SEM. FIG. 19 shows that the highest bioadhesion was present in formulations that contained chitosan, which may be due to their positive charge that increase their reaction with the negatively charged mucin and so improve their mucoadhesion.

Particle Size, Poly Dispersity Index (PDI) and Zeta Potential Determination

The particle size, PDI and zeta potential of the formulations were measured using zetasizer nano-ZS after suitable sample dilution (1:100 for particle size and PDI and 1:1000 for zeta potential). The zetasizer data of the MEs are listed in Table 3 as mean±SEM of at least 3 readings. The particle size data show that all formulations possessed a tiny particle size (<20 nm) with a very narrow particle size distribution. In an aspect of the invention, this tiny particle size is useful for topical ophthalmic formulations since it does not cause a gritty sensation that may bother the patient and affect his/her compliance to use the medication and the tiny particle size can improve drug penetration through the cornea by passive diffusion. The zeta potential charge differed according to the polymer used, which is positive for chitosan and negative for both CARBOPOL® (carbomer) and alginate MEs.

TABLE 3

Particle size, PDI and zeta potential of different MEs.

| Formulation | Particle size (nm) | | PDI | | Zeta potential (mV) | |
| --- | --- | --- | --- | --- | --- | --- |
| | Blank | Medciated | Blank | Medicated | Blank | Medicated |
| Aliginate ME | 16.8 ± 0.3 | 16.5 ± 0.2 | 0.34 ± 0.0 | 0.34 ± 0.0 | −26.8 ± 0.8 | −26.7 ± 1.7 |
| Chitosan ME | 17.4 ± 0.0 | 17.4 ± 0.3 | 0.36 ± 0.0 | 0.37 ± 0.0 | 15.9 ± 3.3 | 10.2 ± 2.3 |
| CARBOPOL® (carbomer) ME | 16.0 ± 0.2 | 15.4 ± 0.1 | 0.26 ± 0.0 | 0.26 ± 0.0 | −30.1 ± 2.2 | −26.3 ± 1.0 |

Mucoadhesion Study

The formulations' mucoadhesion force was evaluated using an already published method. (Gallo EEHaJM 1990. A simple rheological method for the in vitro assessment of mucin-polymer bioadhesive bond strength. Pharmaceutical research 7(5):491-495; Mayol L, Quaglia F, Borzacchiello A, Ambrosio L, La Rotonda M I 2008. A novel poloxamer/hyaluronic acid in situ forming hydrogel for drug delivery: rheological, mucoadhesive and in vitro release properties. Eur J Pharm Biopharm 70(1):199-206; Tayel S A, El-Nabarawi M A, Tadros M I, Abd-Elsalam W H 2013. Promising ion-sensitive in situ ocular nanoemulsion gels of terbinafine hydrochloride: design, in vitro characterization and in vivo estimation of the ocular irritation and drug pharmacokinetics in the aqueous humor of rabbits. Int J Pharm 443(1-2):293-305.). Briefly, preheated formulations (at 35° C.) were mixed with 15% dispersion of gastric mucin (at 35° C.) in 1:1 ratio. The viscosities of the formulations, mucin and their mixtures were measured using Brookfield cone and plate rotary viscometer at 35° C. The change in the mixture viscosities were translated to bioadhesion force using the following equations:

Ex Vivo Characterization or Corneal Permeability Study

Figure 20:
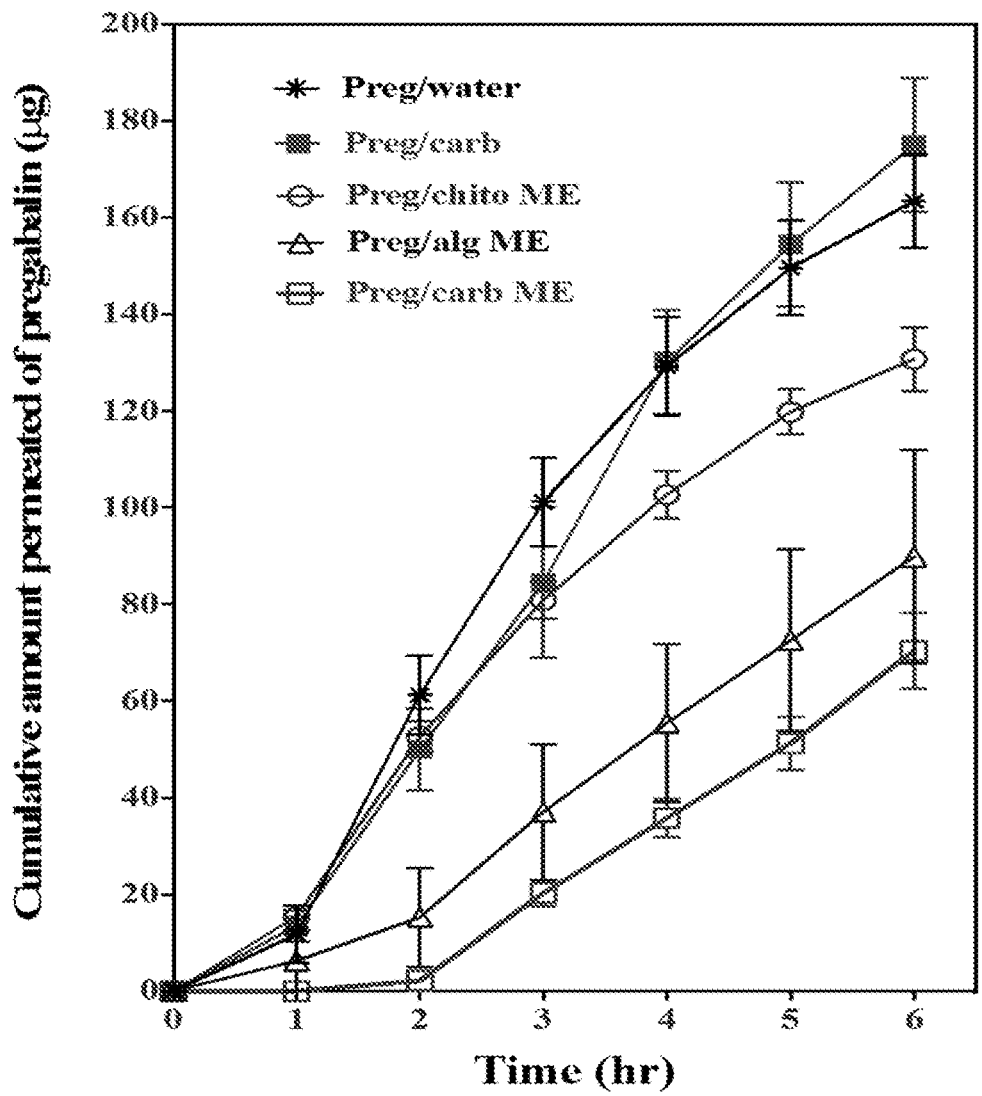
FIG. 20: Corneal permeability profiles of pregabalin formulations that demonstrate that the ME sustain the high corneal permeability of pregabalin.

Modified Franz diffusion cells were used for corneal drug permeability studies for different formulations. The modified Franz diffusion cell consists of two vertically connected chambers (donor and receptor chambers) attached to each other through a spherical junction that is suitable for spherical tissues (i.e. cornea). The volume of the donor chamber was 0.5 ml and that of the receptor chamber was 5 ml. The receptor chamber was stirred at 50 rpm by the aid of a magnetic stir bar to allow continuous mixing of the chamber contents. The orifice at the junction between the two chambers has a 9 mm diameter at which the corneal tissue was fixed and the drug allowed to diffuse. One hundred microliters of each formulation was placed in the donor chamber. The receptor chamber was filled by 5 ml of BSS-Plus (balanced salt solution-plus) and the whole cell was surrounded by a warm water jacket to maintain the temperature at 35° C. A sample of 0.5 ml was withdrawn from the receptor chamber every 1 h for a total period of 6h and replaced by a fresh BSS-Plus that maintained at 35° C. The collected samples were assayed for their drug contents using a standard HPLC protocol. The experiment was repeated six times and the results were calculated as mean±SEM. The cumulative amount that permeated through the cornea for six hours for each formulation was plotted and the data shown in FIG. 20. Pregabalin is a BCS class-I drug, which means that it is a highly permeable and highly soluble drug. FIG. 20 and Table 4 show that the ME-free formulation (Preg/water and Preg/CARBOPOL® (carbomer)) possessed a higher permeation rate than the formulation containing ME. This is because of the natural ability of the drug to rapidly permeate through the cornea, which when given on its own, does not allow for a sustained release of the drug over time. All formulations containing ME possessed a lower permeation rate than Pregabalin alone. By using any formulations containing ME and the drug, sustained release is possible. Upon comparing the ME formulations, it was found that the formulation that contained CARBOPOL® (carbomer) possessed the lowest permeation rate among all tested formulations. This experiment confirmed the in vitro release data that an ME can sustain pregabalin release for once daily application.

TABLE 4

In vitro transcorneal permeability parameters of pregabalin ME and control

| Formulation | Rate of permeation (dM/dt) | Flux (µg/cm$^2$/min) | Permeability coefficient (P) x10$^{-4}$ |
|---|---|---|---|
| PRG in water | 0.285 ± 0.1 | 0.45 ± 0.13 | 7.5 ± 2.2 |
| PRG in CARBOPOL ® (carbomer) | 0.374 ± 0.15 | 0.59 ± 0.24 | 9.8 ± 3.9 |
| PRG chitosan ME | 0.233 ± 0.06 | 0.37 ± 0.10 | 6.1 ± 1.7 |
| PRG sod. alginate ME | 0.287 ± 0.18 | 0.45 ± 0.28 | 7.5 ± 4.7 |
| PRG CARBOPOL ® (carbomer) ME | 0.288 ± 0.08 | 0.45 ± 0.13 | 7.6 ± 2.2 |

Figure 21:
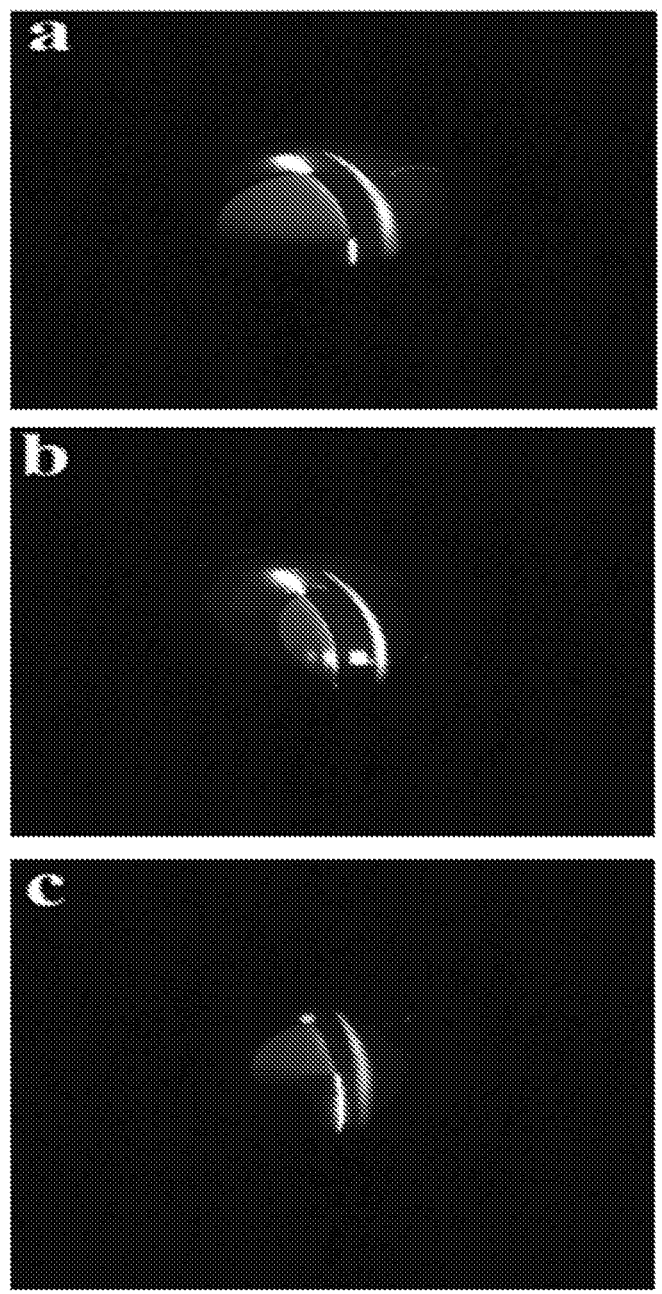
FIG. 21: Slit-lamp examination after application of different pregabalin MEs: (a) CARBOPOL® (carbomer), (b) alginate, or (c) chitosan.

In Vivo Characterization or IOP-Lowering Study on Dutch Belted Rabbits
Formulation Safety The safety of ME formulations was tested by installation of 100 µl of each formulation in the lower conjunctival sac of the right eye of Dutch Belted rabbits (n=3) while the left eye served as a control. Eyes were examined every hour for any sign of irritation such as redness, tearing, conjunctival swelling or corneal swelling. Slit-lamp examination was performed for all rabbit eyes at the end at the experiment. FIG. 21 are exemplary photographs of slit-lamp examination after the application of the ME formulations. The figure shows that no signs of irritation were detected: the cornea was clear and there was no swelling, the lens was clear, and the aqueous humor was clear with no cells or flare.

Formulation Efficacy

The IOP-lowering effect of the formulations was determined using a single dose-response design. Dutch Belted (DB) rabbits (n=3) were used for this study, during which each rabbit received 100 µl of the medicated formulation in the lower conjunctival sac of its right eye while the left eye served as a control by receiving 100 µl of the blank formulation. The intraocular pressure (IOP) was measured using Tonopen (Tono-pen AVIA Vet, Reichert) immediately before the application of the formulation (baseline) and at predetermined time intervals until it returned back to its baseline value.

Figure 22:
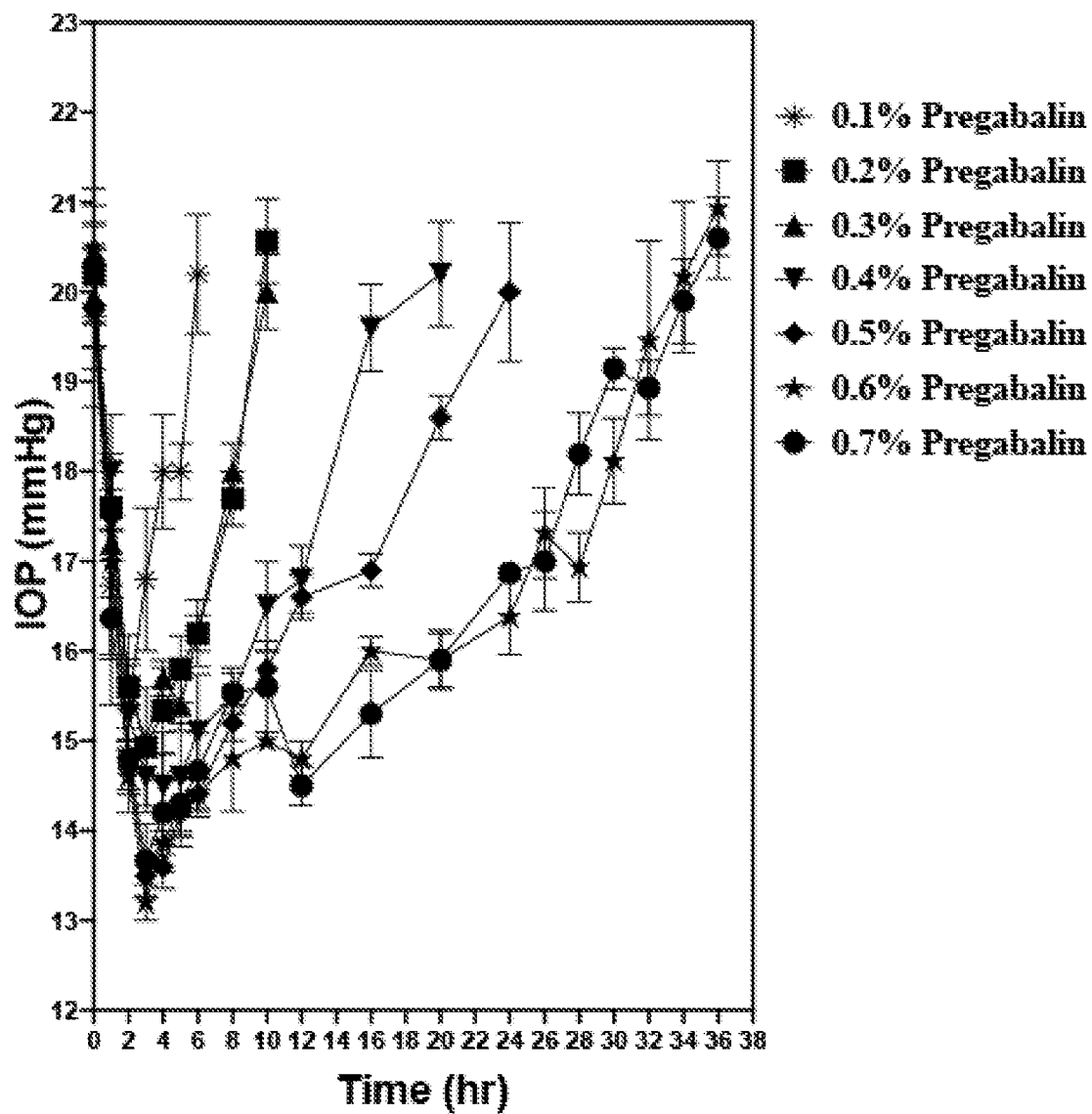
FIG. 22: IOP profiles of Dutch belted rabbits after topical application of pregabalin in CARBOPOL® (carbomer) ME at concentrations ranging from 0.1-0.7% (n=5).

FIG. 22 shows the IOP profile of DB rabbits after application of the CARBOPOL® (carbomer) ME formulation containing different concentrations of pregabalin (0.1-0.7%). There was a dose dependent increase in the IOP-lowering efficacy of the formulations until 0.6%. There was no significant difference between 0.6% and 0.7% pregabalin. Therefore 0.6% pregabalin was selected as the minimum dose that gave the maximum response.

To identify the formulation that provided the maximum IOP-lowering efficacy, we performed a single dose-response design study using Dutch Belted rabbits by varying the external aqueous phase of the ME. Table 5 lists the calculated pharmacodynamic parameters based on the IOP profiles and Table 6 provides the statistical comparisons. Based on the results, the CARBOPOL® (carbomer) ME provides good IOP-reduction and extended effect.

TABLE 5

Pharmacodynamic parameters after application of 0.6% pregabalin in different ME of different formulations to Dutch belted rabbits.

| PD parameters (mean ± SEM) | Ophthalmic formulations | | | |
|---|---|---|---|---|
| | Carb ME | Sod alg ME | Chitosan ME | Preg in Carb |
| Baseline IOP (mmHg) | 21.4 ± 0.7 | 20.9 ± 0.2 | 21.2 ± 0.4 | 22.1 ± 0.4 |
| I$_{max}$ (mmHg) | 13.1 ± 0.7 | 13.7 ± 0.4 | 14.2 ± 1.2 | 16.2 ± 0.4 |
| IOP reduction (mmHg) | −8.3 ± 0.2 | −7.2 ± 0.5 | −7.0 ± 1.5 | −5.9 ± 0.8 |
| % IOP Reduction | 38.7 ± 1.3 | 34.4 ± 2.2 | 32.8 ± 6.6 | 26.6 ± 3.1 |
| T$_{max}$ (h) | 3.3 ± 0.9 | 3.7 ± 0.3 | 4.0 ± 1.0 | 3.3 ± 1.4 |
| T$_{end}$ (h) | 32.7 ± 1.3 | 24.0 ± 0.0 | 20.0 ± 0.0 | 10.0 ± 0.0 |
| AUC (mmHg · h) | 169.9 ± 13.4 | 80.7 ± 4.6 | 69.5 ± 14.2 | 39.0 ± 4.0 |

TABLE 6

Statistical comparisons among different pregabalin ME eye drops and the control after application of a single dose

| Pharmacodynamic Parameters | Overall P value | Carb ME vs Sod. Alg ME | Carb ME vs Chitosan ME | Carb ME vs Preg in Carb | Sod. alg ME vs Chitosan ME | Sod. alg ME vs Preg in Carb | Chitosan vs PRg in Carb |
|---|---|---|---|---|---|---|---|
| % Reduction in IOP | 0.2504 | >0.05 | >0.05 | >0.05 | >0.05 | >0.05 | >0.05 |
| T$_{max}$ (h) | 0.9567 | >0.05 | >0.05 | >0.05 | >0.05 | >0.05 | >0.05 |
| T$_{end}$ (h) | <0.0001 | <0.001 | <0.0001 | <0.0001 | <0.05 | <0.0001 | <0.0001 |
| AUC$_{total}$ (% h) | 0.0001 | <0.01 | <0.001 | <0.0001 | >0.05 | >0.05 | >0.05 |

Figure 23:
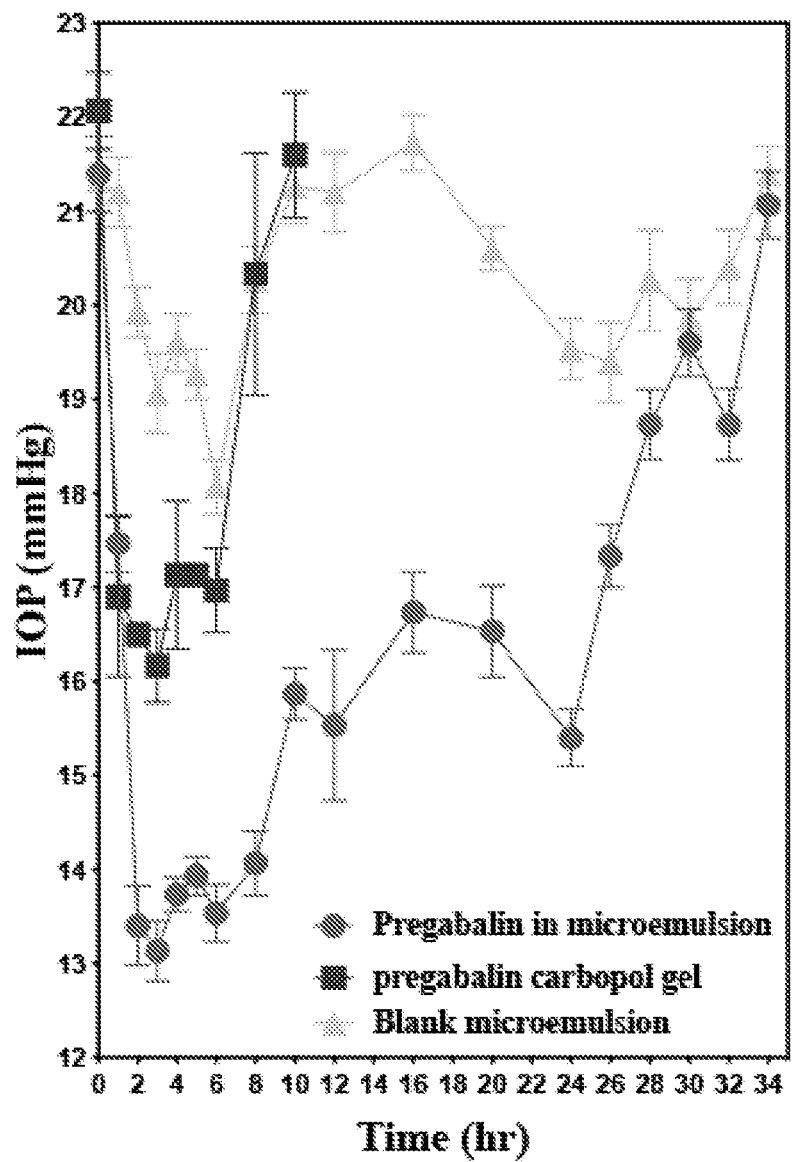
FIG. 23: IOP profiles from Dutch belted rabbits after topical application of blank ME, pregabalin in CARBOPOL® (carbomer) gel, and pregabalin in CARBOPOL® (carbomer) ME (n=5).

FIG. 23 shows a comparison between both CARBOPOL (carbomer) formulations (gel and ME) which demonstrates that the ME greatly extends the duration of the drug effect. Evaluation of the formulation was achieved by comparing between their pharmacodynamics (PD) parameters, which included percentage of the maximum reduction in IOP (% I$_{max}$), time at which maximum IOP reduction occurs (T$_{max}$), time required for IOP to return back to its baseline value (T$_{end}$) and the area under the IOP-time curve (AUC).

Tachyphylaxis Study of Pregabalin CARBOPOL® ME

Figure 24:
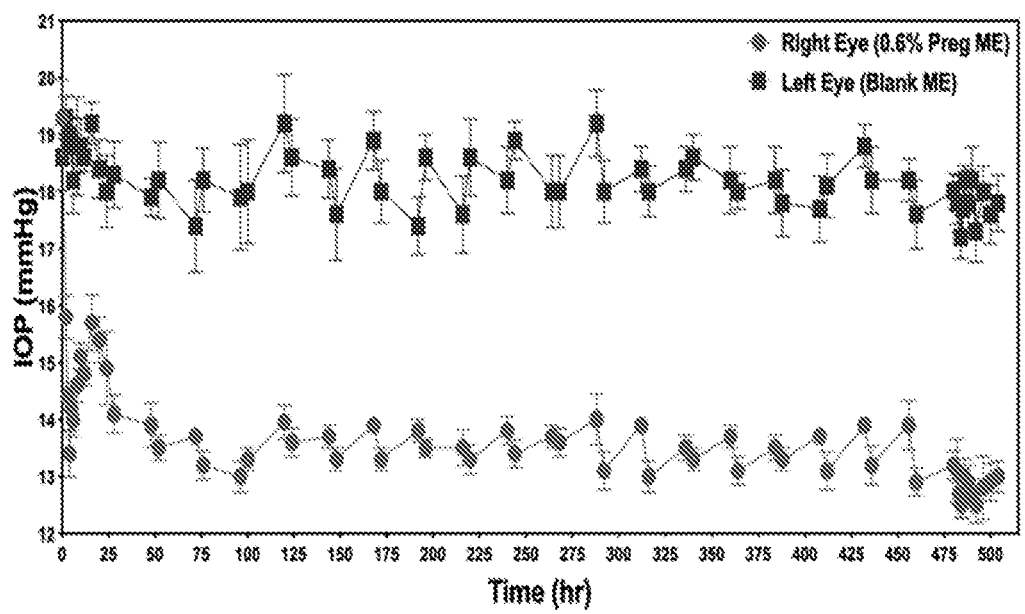
FIG. 24: IOP profiles from Dutch belted rabbits during a 21-day tachyphylaxis study using pregabalin CARBOPOL® (carbomer) ME (n=5).
Figure 25:
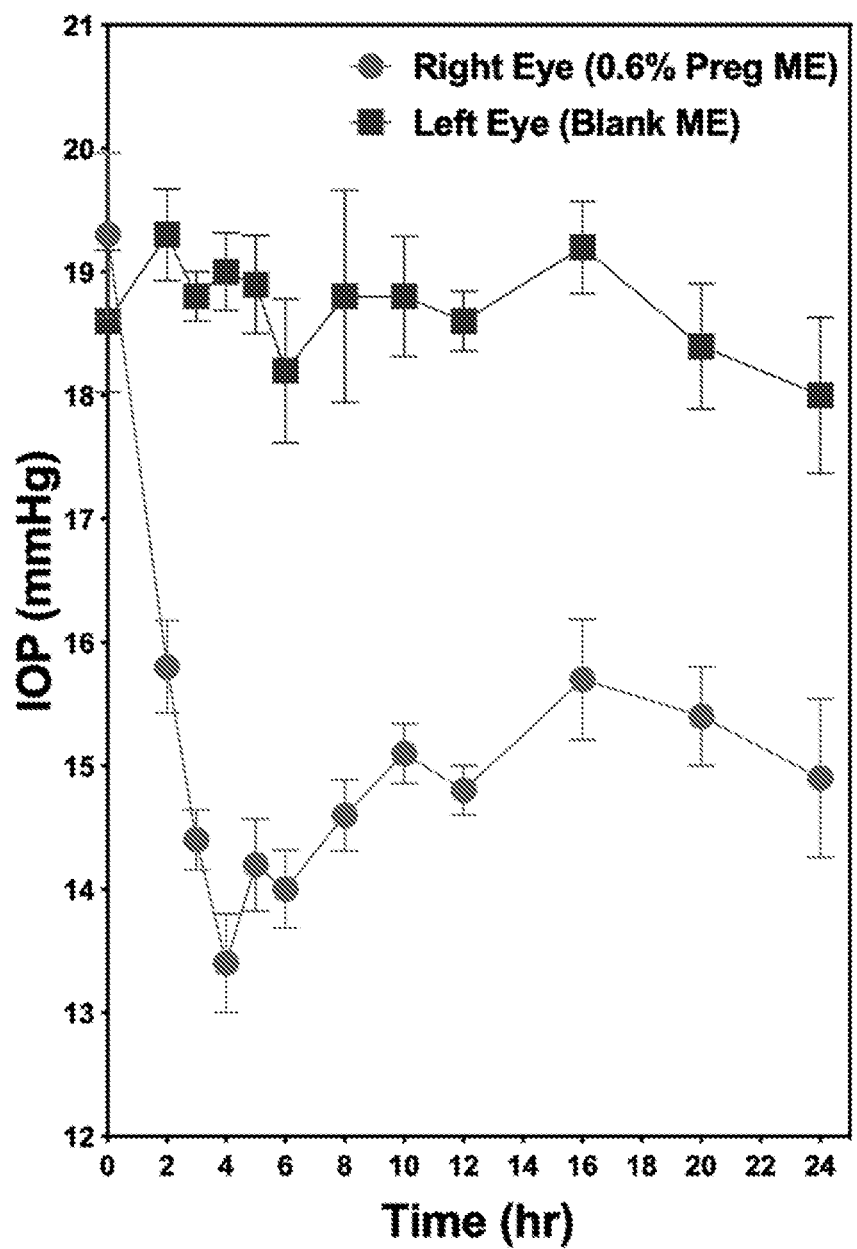
FIG. 25: IOP profiles from Dutch belted rabbits during the first 24 hours of a 21-day tachyphylaxis study using pregabalin CARBOPOL® (carbomer) ME (n=5).
Figure 26:
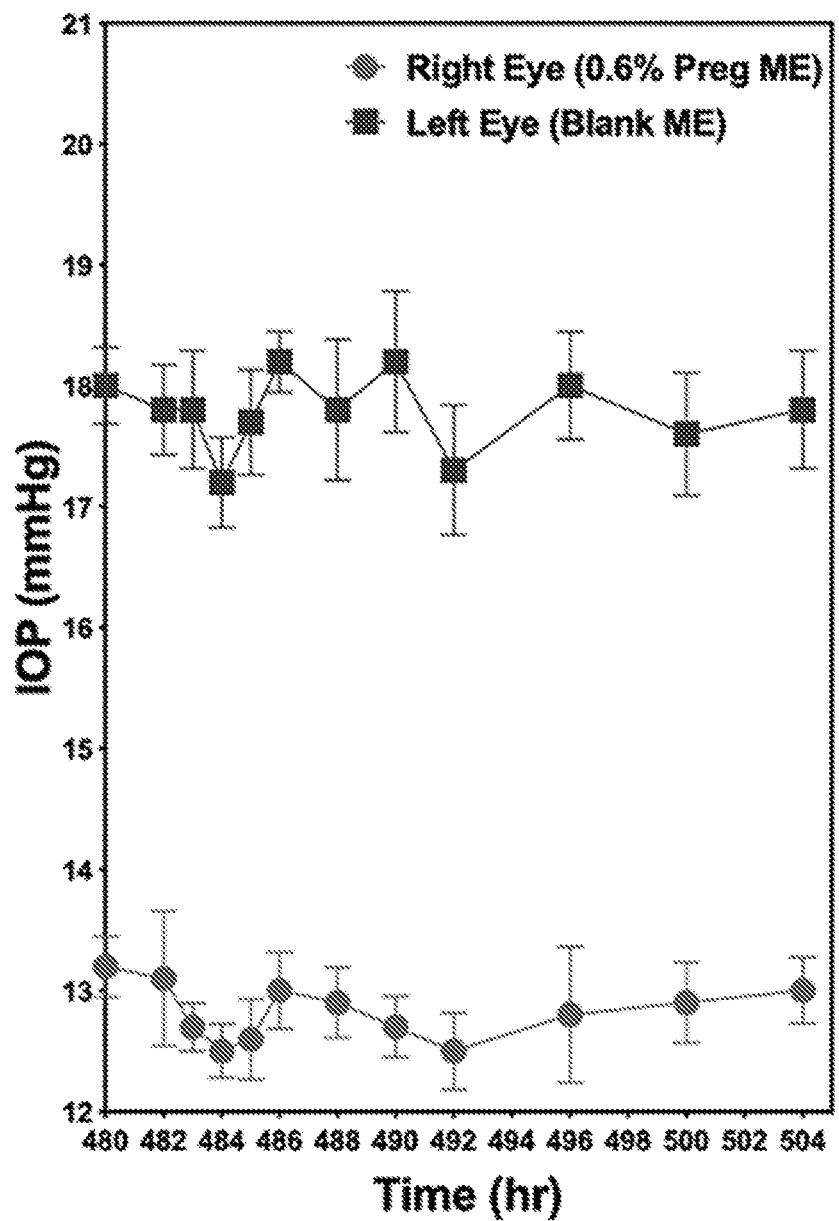
FIG. 26: IOP profiles from Dutch belted rabbits during the last 24 hours of a 21-day tachyphylaxis study using pregabalin CARBOPOL® (carbomer) ME (n=5).

To determine if the pregabalin CARBOPOL® (carbomer) ME was able to maintain IOP at a reduced level after multiple dosings, we performed a tachyphylaxis study for 21 days. A single drop of pregabalin loaded ME formulation was instilled into the right eye of Dutch belted rabbits and blank ME was instilled into the left eye at 8 am each day for 3 weeks. IOP was measured every 1-2 hours on days 1 and 21, while on all other days it was measured twice per day. FIG. 24 demonstrates that the IOP of the medicated eye was reduced by 30.7% at the $T_{max}$ of day 1. IOP started to return toward baseline IOP but was still reduced by 20.5% by 24 hours after receiving the first dose (FIG. 25). After receiving the $2^{nd}$ dose of ME formulation, IOP was maintained in a normal physiological range between 12 and 13 mmHg throughout the duration of the study (FIGS. 24 and 26).

Efficacy of Other Gabapentinoid Drugs

To determine if other members of the gabapentinoid drug family are also efficacious in reducing IOP, we compared the efficacy of 0.9% pregabalin, 0.9% 2-phenylglycine and 0.9% gabapentin in 2% HPMC viscous eye drops in C57Bl/6 J mice.

Figure 27:
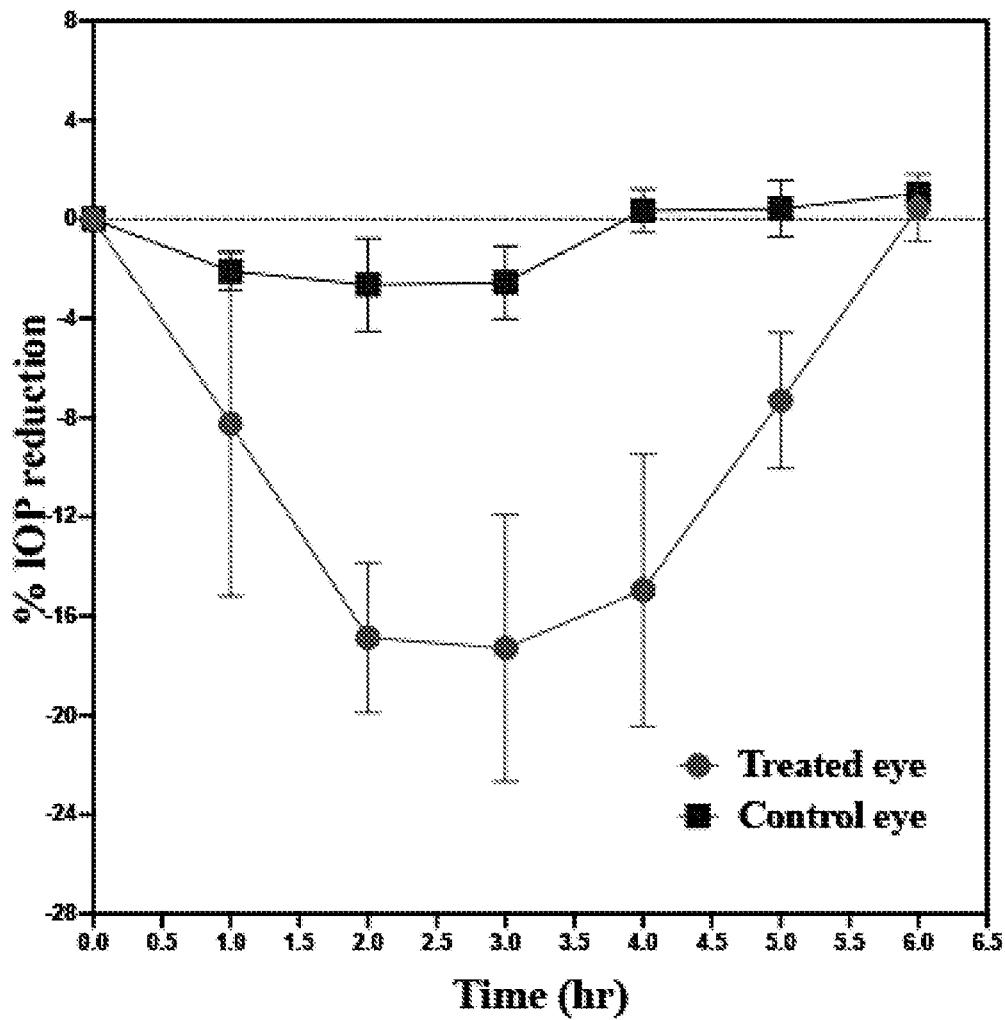
FIG. 27: IOP profiles from B6 mice after topical application of 0.9% pregabalin in 2% HPMC viscous eye drops (n=5).
Figure 28:
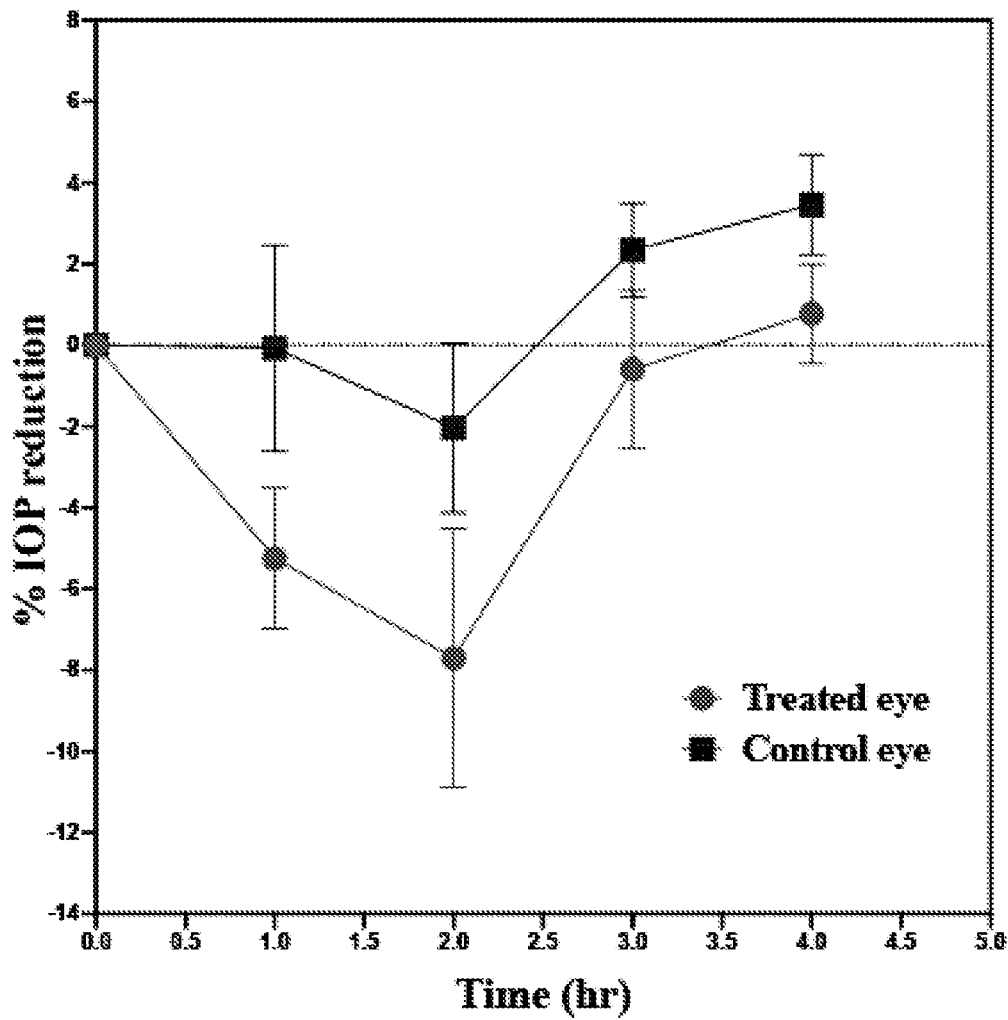
FIG. 28: IOP profiles from B6 mice after topical application of 0.9% 2-phenylglycine in 2% HPMC viscous eye drops (n=5).
Figure 29:
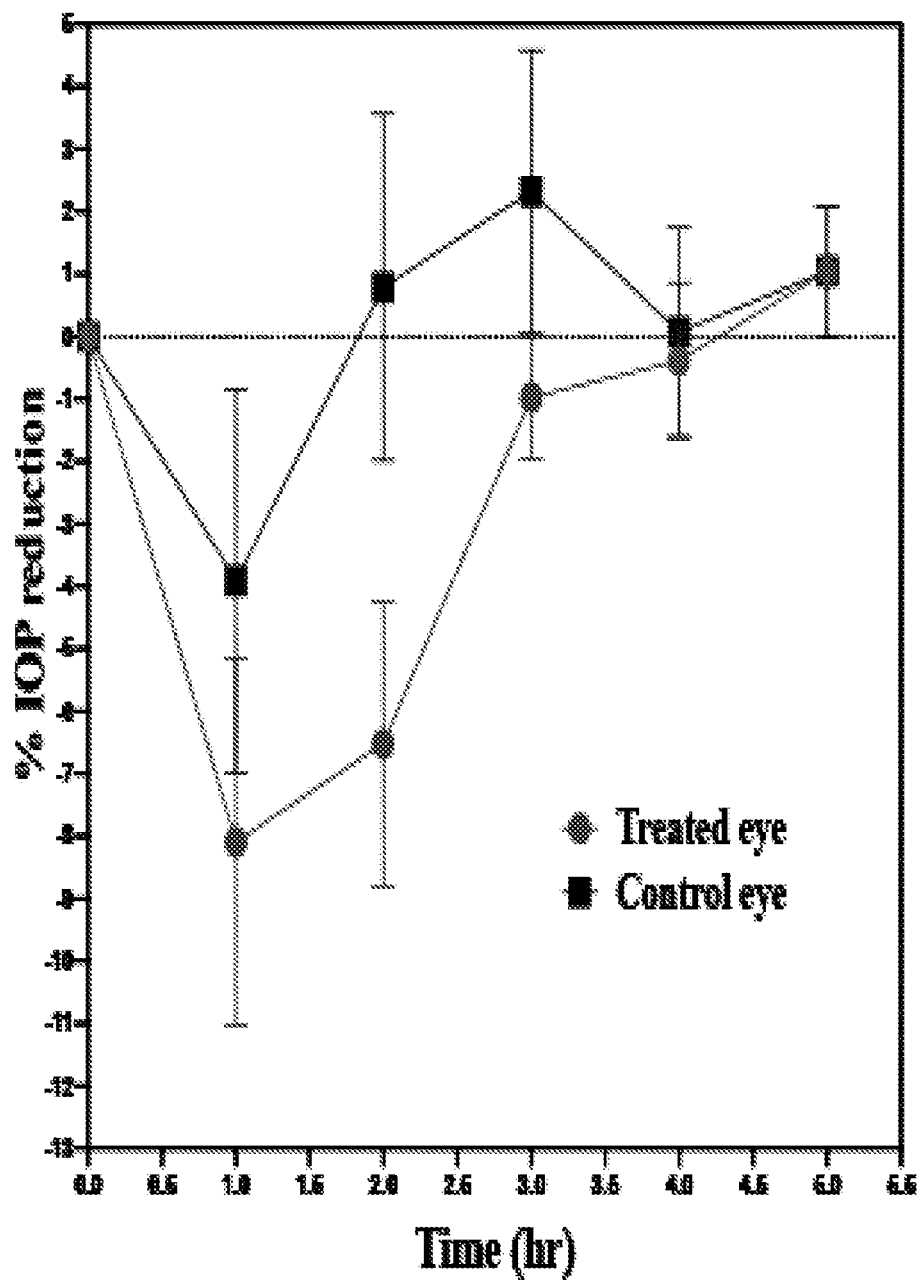
FIG. 29: IOP profiles from B6 mice after topical application of 0.9% gabapentin in 2% HPMC viscous eye drops (n=5).

Pregabalin in viscous eye drops gave a maximum IOP reduction of 17.3% that returned to baseline by 6 hrs with an area under the curve of 65% hr (FIG. 27). 2-phenylglycine (FIG. 28) and gabapentin (FIG. 29) were not as efficacious as pregabalin although they both had maximum IOP reductions of −8% and areas under the curve of −14% hr. These data demonstrate that although they are not as effective in reducing IOP, both 2-phenylglycine and gabapentin are able to induce an IOP-lowering response.

Pregabalin CARBOPOL® ME Non-Inferiority Test

Figure 30:
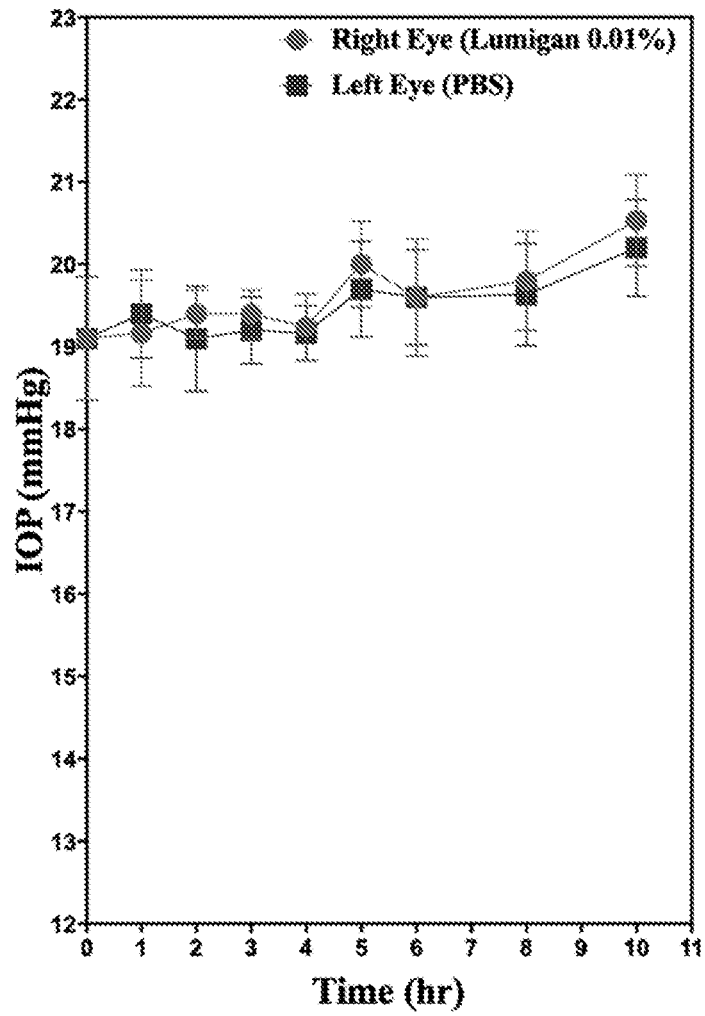
FIG. 30: IOP profiles from Dutch belted rabbits after topical application of Lumigan, 0.01% dosed at 9 am (n=5).
Figure 31:
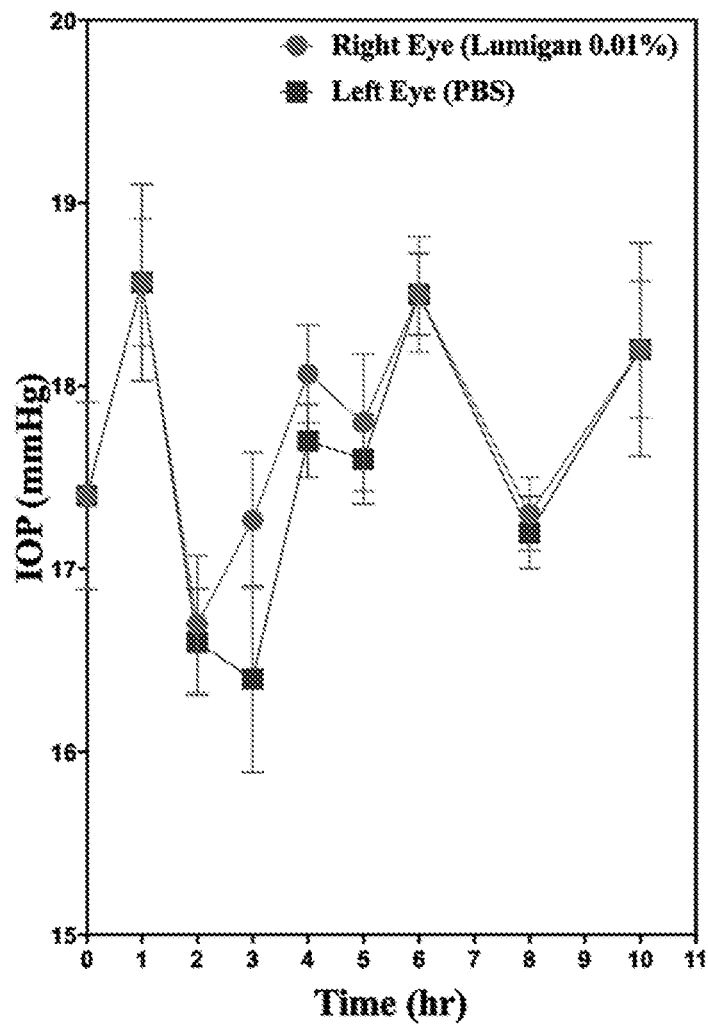
FIG. 31: IOP profiles from Dutch belted rabbits after topical application of Lumigan, 0.01% dosed at 9 pm (n=5).

To determine how our pregabalin ME formulation compared to a market leader IOP-lowering drug, we evaluated Lumigan 0.01% in our same Dutch belted rabbit formulation. In humans, Lumigan is dosed at night before bed. We evaluated dosing at 9 am and 9 pm. In rabbits dosed both at 9 am (FIG. 30) and 9 pm (FIG. 31), there was no difference in IOP between treated with Lumigan or vehicle. The time of dosing did not affect the lack of IOP lowering response. Therefore, our pregabalin ME is not inferior to the market leader IOP-lowering drops.

epithelium. Ribavirin is a synthetic nucleoside analogue. Its chemical name is 113-D-ribofuranosyl-1H-1,2,4-triazole-3-carboxamide, its empirical formula is $C_8H_{12}N_4O_5$ and the molecular weight is 244.21. Ribavirin is a white, crystalline powder. It is freely soluble in water, like pregabalin.

Drug Release Study of Ribavirin

Figure 32:
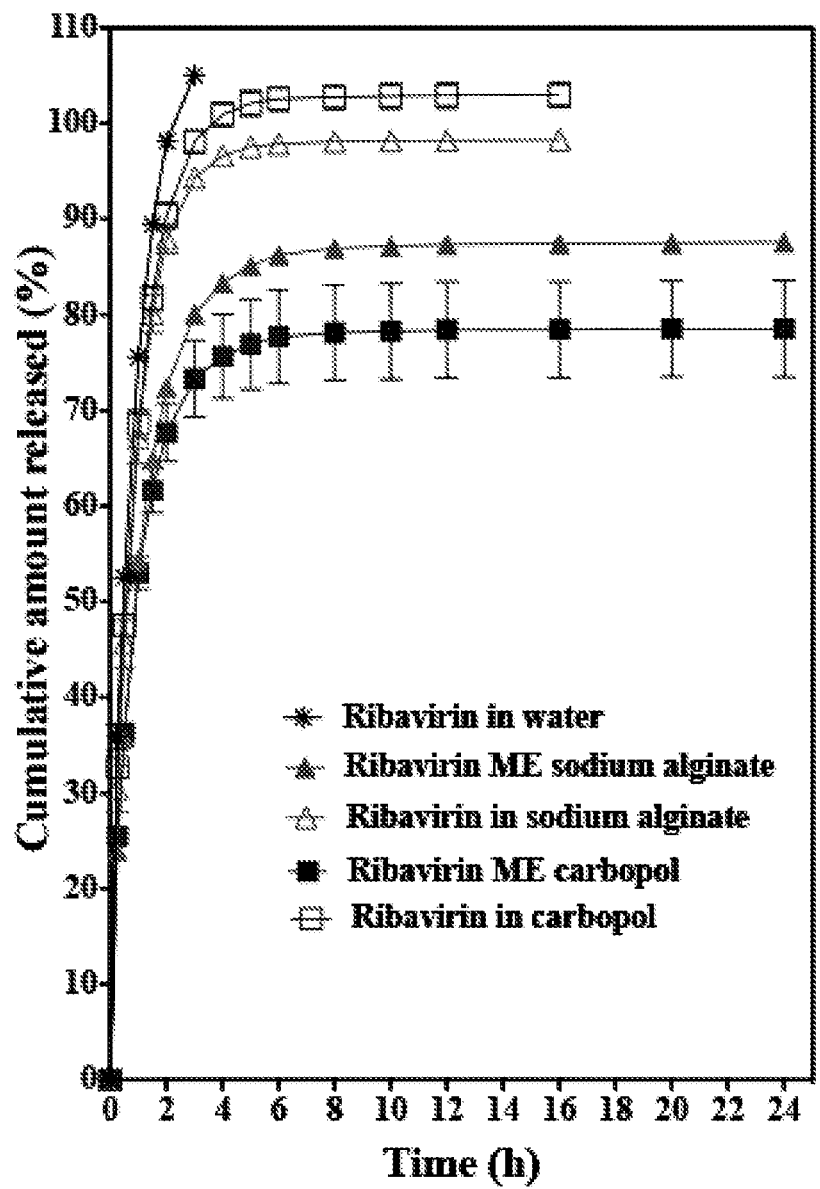
FIG. 32: Ribavirin release profiles from different formulations show the sustained release behavior of MEs, which is especially clear in CARBOPOL® (carbomer) ME that gave a steady release rate that lasted for up to 24 h.

The sustained release behavior of ribavirin from different formulations was studied using identical methods detailed above for pregabalin. The release profiles (FIG. 32) demonstrate that all control formulations exhibited fast release behaviors that released 100% of the drug content within 3-4 h. In contrast, the tested MEs exhibited sustained release behaviors that lasts for up to 24 h.

Cell Toxicity Study of Ribavirin ME Formulations

Figure 33:
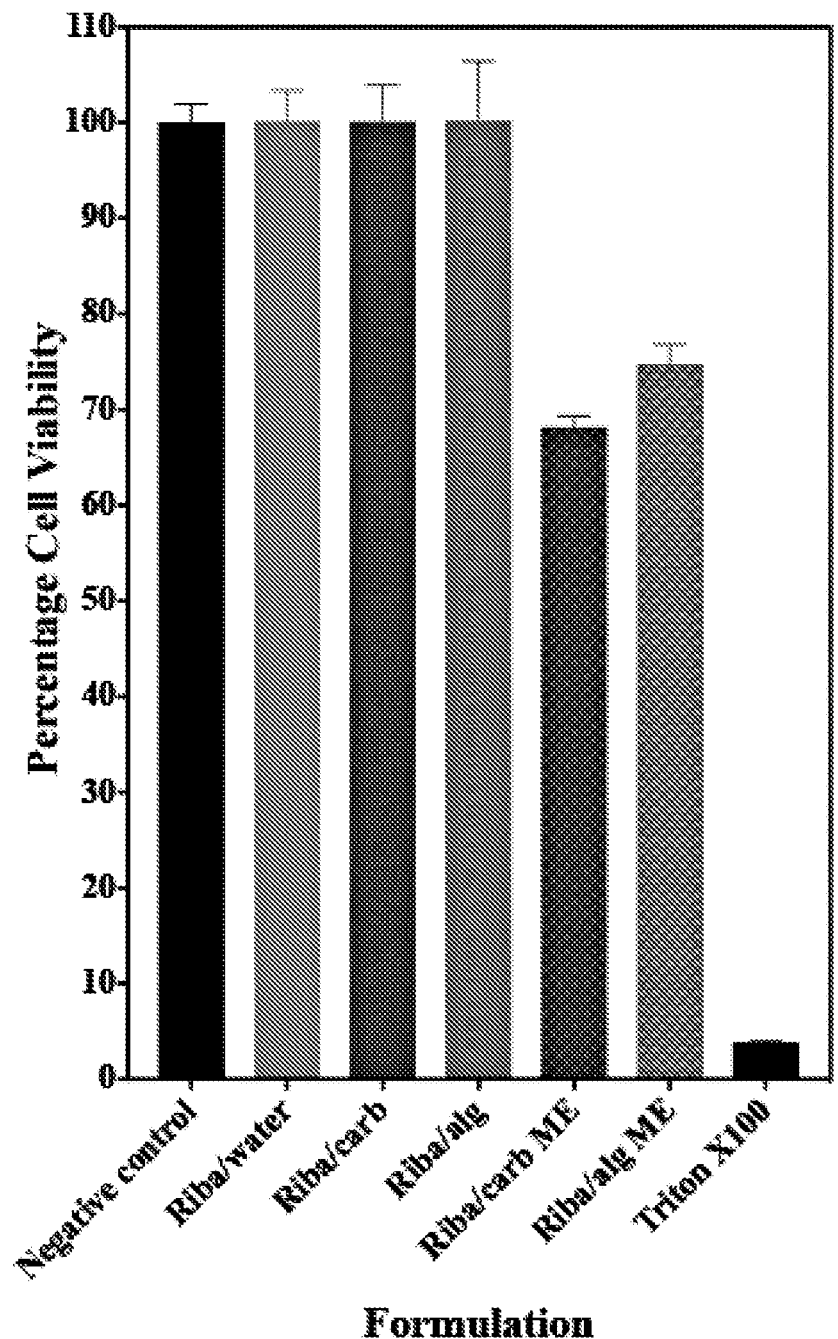
FIG. 33: Histograms of cytotoxicity of different formulations containing ribavirin show the safety of our formulations to human corneal epithelial cells.

In-vitro cell toxicity of the formulations was tested by MTT assay method using identical methods detailed above for pregabalin. FIG. 33 shows that the formulations are safe and nontoxic for the corneal epithelial cells at the therapeutic dose. The experiment was repeated 8 times for each formulation and the results were calculated as mean±SEM.

Viscosity Study of Ribavirin ME Formulations

Figure 34:
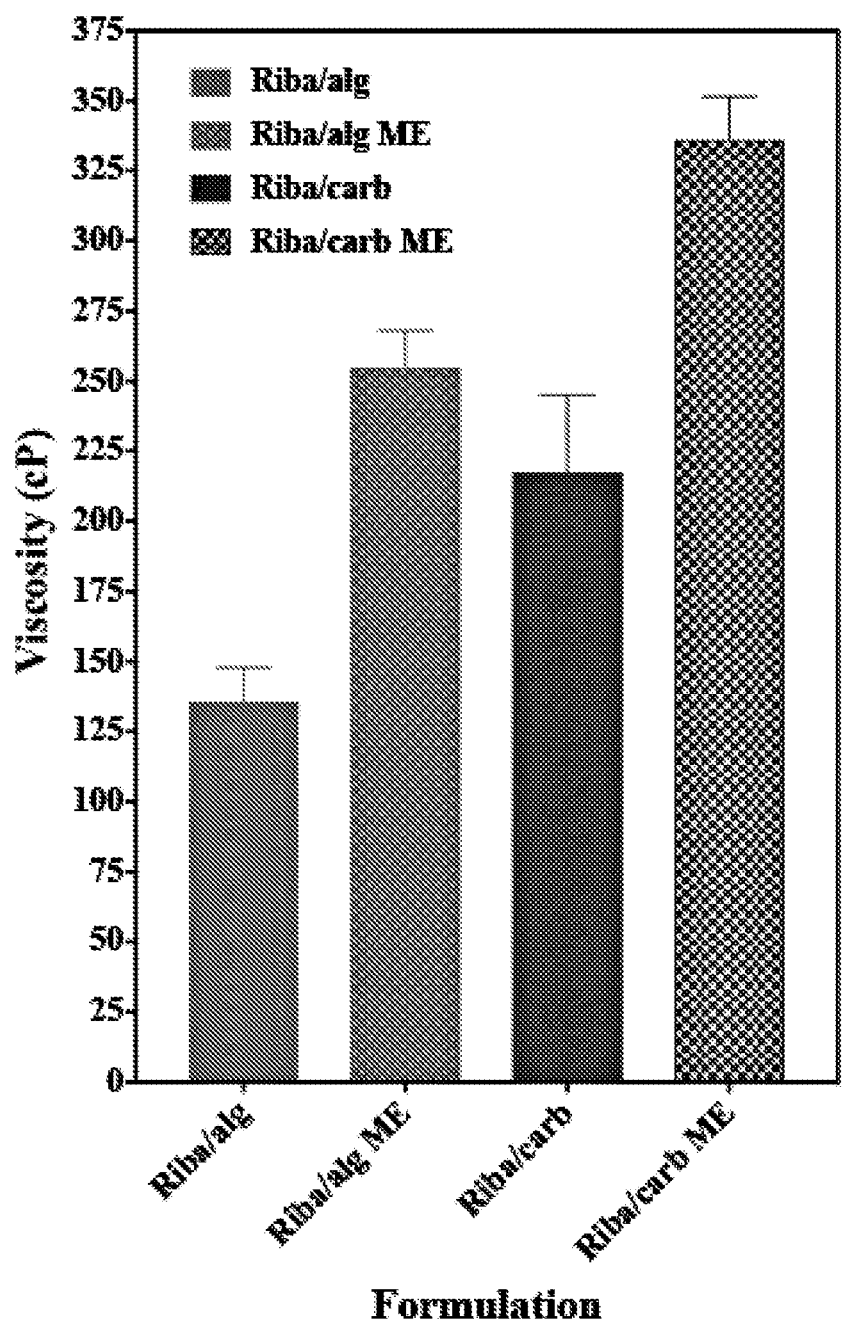
FIG. 34: Histograms of viscosity show that the ribavirin formulation containing CARBOPOL® (carbomer) possesses the highest viscosity value, which will allow it to remain on the eye for longer time.

Viscosity of the formulations was measured using identical methods detailed above for pregabalin. FIG. 34 shows that the formulations containing CARBOPOL® (carbomer) possessed the highest viscosity, which allows them to remain inside the eye for longer time.

Mucoadhesion Study of Ribavirin ME Formulations

Figure 35:
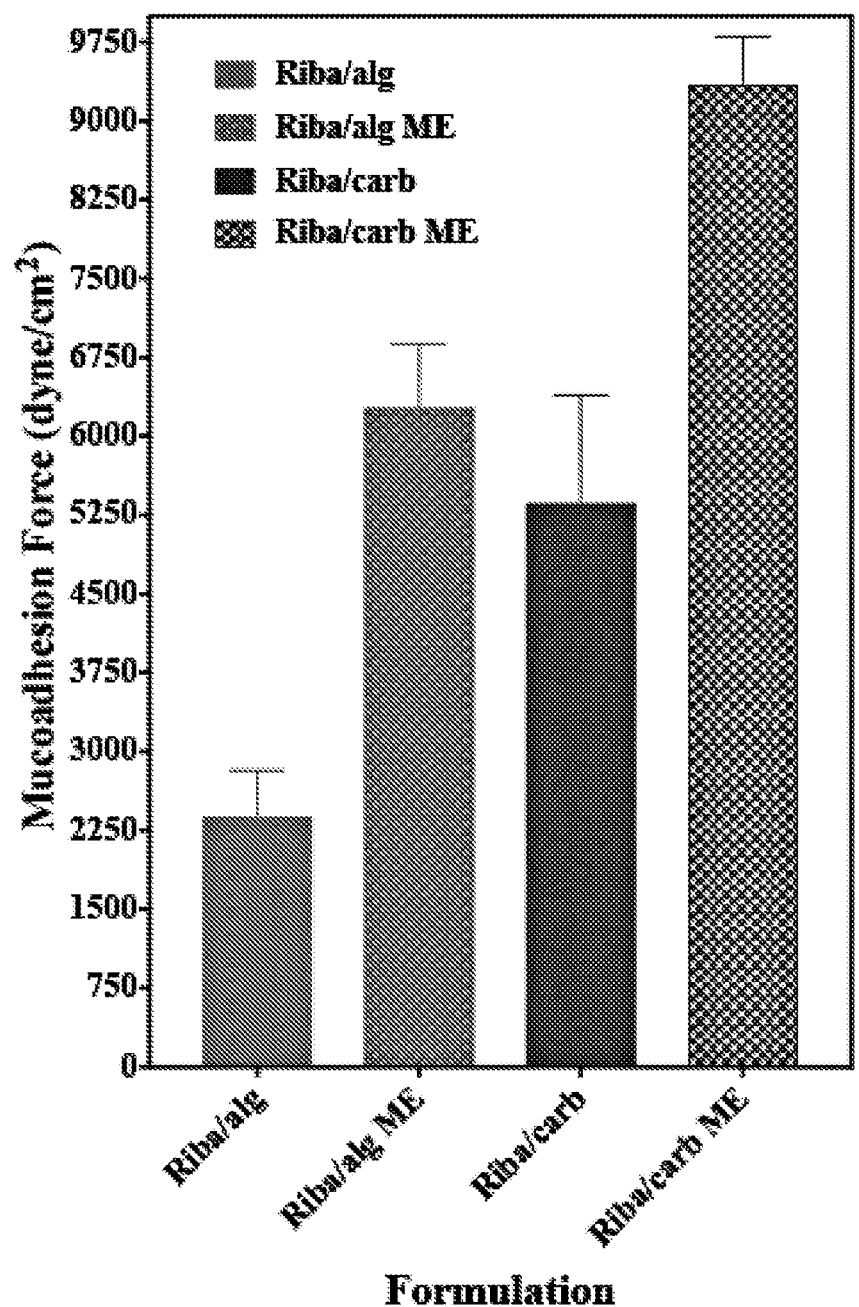
FIG. 35: Histograms of formulation mucoadhesion show that the ribavirin CARBOPOL® ME formulation possesses higher mucoadhesion than the other formulations.

The formulations mucoadhesion force was evaluated using identical methods detailed above for pregabalin. The experiment was repeated three times and the results were calculated as mean±SEM. FIG. 35 shows that the highest bioadhesion was present in formulations that contained CARBOPOL® (carbomer).

Particle Size, Poly Dispersity Index (PDI) and Zeta Potential Determination of Ribavirin ME Formulations The particle size, PDI and zeta potential of the formulations of Ribavirin formulations were measured using identical methods detailed above for pregabalin. The zetasizer data of the MEs are listed in Table 7 as mean±SEM of at least 3 readings. The particle size data show that all formulations possessed a tiny particle size (<20 nm) with a very narrow particle size distribution.

TABLE 7

Particle size, PDI and zeta potential of Ribavirin containing MEs

| Formulation | Particle size (nm) | | PDI | | Zeta potential (mV) | |
| --- | --- | --- | --- | --- | --- | --- |
| | Blank | Medicated | Blank | Medicated | Blank | Medicated |
| Aliginate ME | 10.8 ± 0.3 | 10.7 ± 0.04 | 0.304 ± 0.0 | 0.303 ± 0.0 | −19.1 ± 0.96 | −20.4 ± 1.9 |
| CARBOPOL® (carbomer) ME | 9.2 ± 0.1 | 9.1 ± 0.04 | 0.155 ± 0.0 | 0.163 ± 0.0 | −23.7 ± 1.1 | −21.4 ± 1.8 |

Evaluation of ME Compatibility with Other Water Soluble Drugs

Figure 36:
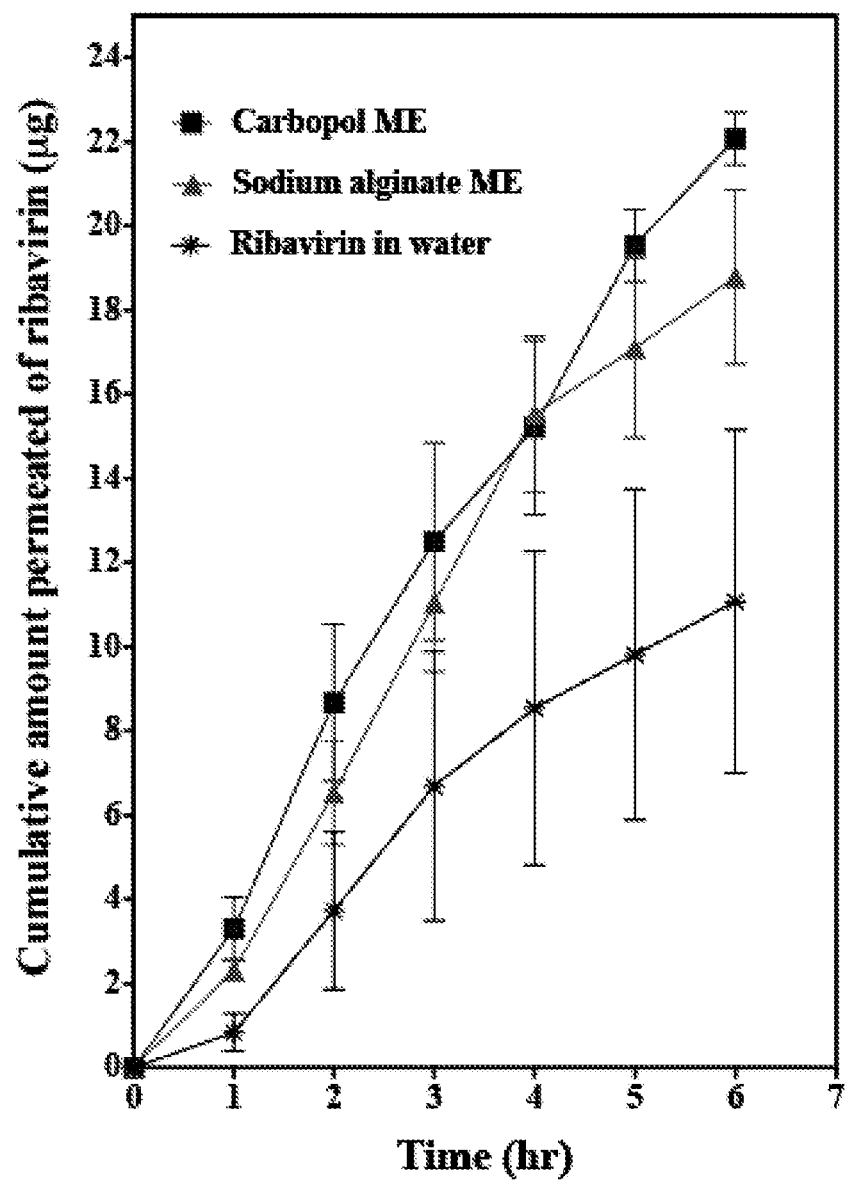
FIG. 36: Corneal permeability profiles of ribavirin formulations demonstrate that the MEs increase the corneal permeability of ribavirin.

To determine if our pregabalin CARBOPOL® (carbomer) ME is compatible with other water-soluble drugs, we synthesized and characterized a ribavirin-loaded CARBOPOL® (carbomer) ME using identical methods. Ribavirin is an antiviral medication used to treat respiratory syncytial virus infection, hepatitis C, and viral hemorrhagic fever. It can also be used to treat viral infections of the eye such as Herpes simplex keratitis, a disease of the corneal Ex Vivo Characterization or Corneal Permeability Study of Ribavirin ME Formulations Ribavirin containing formulations were characterized using identical methods detailed above for pregabalin. The cumulative amount permeated through cornea for six hours for each formulation was plotted and the data shown in FIG. 36 and Table 8. Ribavirin is a BCS class-III drug, which means that it is a not highly permeable, yet it is highly soluble drug. FIG. 36 shows that the ME formulations increased the permeation rate over Ribavirin alone.

TABLE 8

In vitro transcorneal permeability parameters of pregabalin ME and control

| Formulation | Rate of permeation (dM/dt) | Flux ($\mu g/cm^2/min$) | Permeability coefficient (P) $\times 10^{-4}$ |
|---|---|---|---|
| PRG in water | 0.285 ± 0.1 | 0.45 ± 0.13 | 7.5 ± 2.2 |
| PRG in CARBOPOL ® (carbomer) | 0.374 ± 0.15 | 0.59 ± 0.24 | 9.8 ± 3.9 |
| PRG chitosan ME | 0.233 ± 0.06 | 0.37 ± 0.10 | 6.1 ± 1.7 |
| PRG sod. alginate ME | 0.287 ± 0.18 | 0.45 ± 0.28 | 7.5 ± 4.7 |
| PRG CARBOPOL ® (carbomer) ME | 0.288 ± 0.08 | 0.45 ± 0.13 | 7.6 ± 2.2 |

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

We claim:
1. A microemulsion comprising:
   (a) a discontinuous internal phase comprising an aqueous solution encompassed within an internal emulsifier, wherein the aqueous solution comprises pregabalin;
   (b) a continuous oil phase encompassing the internal phase;

(c) an external emulsifier encompassing the oil phase; and
(d) an aqueous phase surrounding the external emulsifier and comprising a hydrogel comprising a mucoadhesive polymer,
wherein the microemulsion is a water-in-oil-in-water microemulsion and comprises globules formed by (a)-(c) that are between about 1 nm and about 50 nm in diameter.

2. The microemulsion of claim 1, wherein the internal emulsifier comprises a surfactant with a hydrophilic-lipophilic balance (HLB) value of 3-7.

3. The microemulsion of claim 2, wherein the surfactant with an HLB value of 3-7 is polyethylene glycol oleyl ether.

4. The microemulsion of claim 1, wherein the internal emulsifier comprises lecithin, diethylene glycol monoethyl ether; mixture of polyethylene glycol (PEG) mono-, di-, tri-esters of stearic acid; mixture of PEG mono-, di-, tri-esters of lauric acid; mixture of PEG mono-, di-, tri-esters of fatty acids $C_8$-$C_{18}$; a propylene glycol ester of a fatty acid; polyethylene glycol lauryl ether; polyethylene glycol oleyl ether; polyethylene glycol hexadecyl ether; sorbitan monopalmitate; sorbitan monostearate; sorbitan monooleate; sorbitan monopalmitate; sorbitan monostearate; sorbitan monooleate; sorbitan monolaurate; tocopherol; a phospholipid; phosphatidylcholine; phosphatidylethanolamine; phosphatidylinositol; or a combination thereof.

5. The microemulsion of claim 1, wherein the aqueous solution is deionized water, saline, phosphate buffered saline, artificial tears, or balanced salt solution.

6. The microemulsion of claim 1, wherein the oil phase comprises medium chain triglycerides of caprylic ($C_8$) and capric ($C_{10}$) acids, fatty acid esters, any natural oil, or a combination thereof.

7. The microemulsion of claim 6, wherein the oil phase comprises an ethyl, propyl, isopropyl, or butyl ester; an ester of caproic acid, caprylic acid, capric acid, lauric acid, palmitic acid, myristic acid, or stearic acid; coconut oil, palm kernel oil, soya bean oil, castor oil, cotton seed oil, corn oil, olive oil; or a combination thereof.

8. The microemulsion of claim 7, wherein the oil phase comprises isopropyl myristate, isopropyl palmitate, isopropyl caproate, isopropyl caprylate, ethyl stearate, or butyl laurate.

9. The microemulsion of claim 1, wherein the oil phase comprises medium-chain triglycerides of caprylic ($C_8$) and capric ($C_{10}$) acids.

10. The microemulsion of claim 1, wherein the external emulsifier comprises a surfactant with a HLB value of 10-16.

11. The microemulsion of claim 10, wherein the surfactant with an HLB value of 10-16 is macrogolglycerol ricinoleate.

12. The microemulsion of claim 1, wherein the external emulsifier comprises a caprylocaproyl polyoxyl-8 glyceride, a polyethylene glycol mono- and/or di-ester of a fatty acid or fatty acid mixture, propylene glycol, an alcohol, polyethylene glycol, macrogolglycerol ricinoleate, glycerol, ethanol, propanol, isopropanol, or a combination thereof.

13. The microemulsion of claim 1, wherein the microemulsion contains 0.5-35% w/w aqueous solution, 0.5-95% w/w oil phase, and 5-99% w/w combined sum of internal emulsifier and external emulsifier.

14. The microemulsion of claim 1, wherein the microemulsion contains 10-30% w/w aqueous solution, 20-40% w/w oil phase, and 40-60% w/w combined sum of internal emulsifier and external emulsifier.

15. The microemulsion of claim 1, wherein the mucoadhesive polymer comprises a polyacrylic acid, alginic acid or a salt thereof, chitosan, dextran, pectin, gelatin, polyvinylpyrrolidone, N-methylpyrrolidone, hyaluronic acid or a salt thereof, gellan gum, xanthan gum, agar, glycocholic acid or a salt thereof, carbomer, or a derivative of any of the foregoing, or a combination thereof.

16. The microemulsion of claim 1, wherein the mucoadhesive polymer comprises carbomer, chitosan or a derivative thereof, or a combination thereof.

17. The microemulsion of claim 1, wherein the microemulsion is formulated as a topical formulation.

18. The microemulsion of claim 1, wherein the internal emulsifier comprises soybean lecithin, egg lecithin, propylene glycol monoester of caprylic acid, propylene glycol monocaproate, propylene glycol monocaprate, propylene glycol monocaprylate, propylene glycol monolaurate, propylene glycol monostearate, propylene glycol monopalmitate, poloxamer 188, polyoxyethylenesorbitan monooleate, polyoxyethylene (10) oleyl ether, or a combination thereof.

19. The microemulsion of claim 1, wherein:
(i) the internal emulsifier comprises polyethylene glycol oleyl ether and soybean lecithin;
(ii) the continuous oil phase comprises medium-chain triglycerides of caprylic ($C_8$) and capric ($C_{10}$) acids; and
(iii) the external emulsifier comprises polyethylene glycol and macrogol glycerol ricinoleate.

20. The microemulsion of claim 1, wherein:
the internal emulsifier comprises a surfactant with a HLB value of 3-7; and
the external emulsifier comprises a hydrophilic surfactant with a HLB value of 10-16.

21. A method for treating glaucoma in a subject in need thereof, comprising administering to the subject an effective amount of the microemulsion of claim 1, wherein administering the microemulsion reduces the intraocular pressure of the subject.

22. The method of claim 21, wherein the microemulsion is administered to one or both eyes of the subject.

23. The method of claim 21, wherein the administering is done once per day.

24. The method of claim 21, wherein the internal emulsifier of the microemulsion comprises a surfactant with a hydrophilic-lipophilic balance (HLB) value of 3-7.

25. The method of claim 24, wherein the surfactant with an HLB value of 3-7 is polyethylene glycol oleyl ether.

26. The method of claim 21, wherein the internal emulsifier of the microemulsion comprises lecithin, diethylene glycol monoethyl ether; mixture of polyethylene glycol (PEG) mono-, di-, tri-esters of stearic acid; mixture of PEG mono-, di-, tri-esters of lauric acid; mixture of PEG mono-, di-, tri-esters of fatty acids $C_8$-$C_{18}$; a propylene glycol ester of a fatty acid; polyethylene glycol lauryl ether; polyethylene glycol oleyl ether; polyethylene glycol hexadecyl ether; sorbitan monopalmitate; sorbitan monostearate; sorbitan monooleate; sorbitan monopalmitate; sorbitan monostearate; sorbitan monooleate; sorbitan monolaurate; tocopherol; a phospholipid; phosphatidylcholine; phosphatidylethanolamine; phosphatidylinositol; or a combination thereof.

27. The method of claim 21, wherein the aqueous solution of the microemulsion is deionized water, saline, phosphate buffered saline, artificial tears, or balanced salt solution.

28. The method of claim 21, wherein the oil phase of the microemulsion comprises medium chain triglycerides of caprylic ($C_8$) and capric ($C_{10}$) acids, fatty acid esters, any natural oil, or a combination thereof.

29. The method of claim 21, wherein the oil phase of the microemulsion comprises medium-chain triglycerides of caprylic ($C_8$) and capric ($C_{10}$) acids.

30. The method of claim 21, wherein the external emulsifier of the microemulsion comprises a surfactant with a HLB value of 10-16.

31. The method of claim 30, wherein the surfactant with an HLB value of 10-16 is macrogolglycerol ricinoleate.

32. The method of claim 21, wherein the external emulsifier of the microemulsion comprises a caprylocaproyl polyoxyl-8 glyceride, a polyethylene glycol mono- and/or di-ester of a fatty acid or fatty acid mixture, propylene glycol, an alcohol, polyethylene glycol, macrogolglycerol ricinoleate, glycerol, ethanol, propanol, isopropanol, or a combination thereof.

33. The method of claim 21, wherein the microemulsion contains 0.5-35% w/w aqueous solution, 0.5-95% w/w oil phase, and 5-99% w/w combined sum of internal emulsifier and external emulsifier.

34. The method of claim 21, wherein the microemulsion contains 10-30% w/w aqueous solution, 20-40% w/w oil phase, and 40-60% w/w combined sum of internal emulsifier and external emulsifier.

35. The method of claim 21, wherein the mucoadhesive polymer of the microemulsion comprises a polyacrylic acid, alginic acid or a salt thereof, chitosan, dextran, pectin, gelatin, polyvinylpyrrolidone, N-methylpyrrolidone, hyaluronic acid or a salt thereof, gellan gum, xanthan gum, agar, glycocholic acid or a salt thereof, carbomer, or a derivative of any of the foregoing, or a combination thereof.

36. The method of claim 21, wherein the mucoadhesive polymer comprises carbomer, chitosan or a derivative thereof, or a combination thereof.

37. The method of claim 21, wherein the microemulsion is formulated as a topical formulation.

38. The method of claim 21, wherein
(i) the internal emulsifier of the microemulsion comprises polyethylene glycol oleyl ether and soybean lecithin;
(ii) the continuous oil phase of the microemulsion comprises medium-chain triglycerides of caprylic ($C_8$) and capric ($C_{10}$) acids; and
(iii) the external emulsifier of the microemulsion comprises polyethylene glycol and macrogol glycerol ricinoleate.

39. The method of claim 21, wherein
the internal emulsifier of the microemulsion comprises a surfactant with a HLB value of 3-7; and
the external emulsifier of the microemulsion comprises a hydrophilic surfactant with a HLB value of 10-16.

* * * * *